(12) United States Patent
Meng et al.

(10) Patent No.: US 11,419,919 B1
(45) Date of Patent: Aug. 23, 2022

(54) HIGH-PURITY ADRENOCORTICOTROPIC HORMONE, ANALOGUE AND A LARGE-SCALE PREPARATION METHOD THEREOF

(71) Applicant: Nanjing Hanxin Pharmaceutical Technology Co., Ltd., Nanjing (CN)

(72) Inventors: Jundong Meng, Nanjing (CN); Kangning Rui, Nanjing (CN); Bin Liu, Nanjing (CN); Yuanyuan Han, Nanjing (CN); Song Chen, Nanjing (CN); Haoning Zhang, Nanjing (CN)

(73) Assignee: Nanjing Hanxin Pharmaceutical Technology Co., Ltd., Nanjing (CN)

( * ) Notice: Subject to any disclaimer, the term of this patent is extended or adjusted under 35 U.S.C. 154(b) by 0 days.

(21) Appl. No.: 17/357,255

(22) Filed: Jun. 24, 2021

(30) Foreign Application Priority Data

Apr. 12, 2021 (WO) ................ PCT/CN2021/086395

(51) Int. Cl.
*A61K 38/35* (2006.01)
*C07K 14/00* (2006.01)

(52) U.S. Cl.
CPC ............ *A61K 38/35* (2013.01); *C07K 14/001* (2013.01)

(58) Field of Classification Search
CPC ....... A61K 38/35; C07K 14/001; C07K 14/00
See application file for complete search history.

(56) References Cited

U.S. PATENT DOCUMENTS

| 3,953,415 A | 4/1976 | Kisfaludy et al. |
| 4,055,524 A | 10/1977 | Colescott et al. |

| 7,264,314 B2 * | 9/2007 | Brennan | .................... A61P 5/42 |
| | | | 530/306 |
| 2006/0128620 A1 * | 6/2006 | Brennan | ................. A61P 15/06 |
| | | | 530/306 |

FOREIGN PATENT DOCUMENTS

| CH | 560182 | * | 3/1975 | .......... C07C 103/52 |
| WO | 2020/186108 A1 | | 9/2020 | |

OTHER PUBLICATIONS

P68000 from UniProt, Integrated into UniProtKB/Swiss-Prot: Jul. 21, 1986, pp. 1-5. (Year: 1986).*
Machine English translation of CH 560182, pp. 1-7. (Year: 1975).*
Medzihradszky, Synthesis of Human ACTH and its Biologically Active Fragments. The Chemistry of Polypeptides. Katsoyannis (Ed.), Springer, Boston. pp. 259-278, Chapter 12, (1973).

* cited by examiner

*Primary Examiner* — Julie Ha
(74) *Attorney, Agent, or Firm* — McCarter & English, LLP; Yu Lu

(57) ABSTRACT

The invention belongs to the technical field of polypeptide preparation methods, and in particular relates to a high-purity ACTH (human sequence) or analogue and large-scale preparation method thereof. The main steps include: amino acids are coupled from the C-terminal to the N-terminal by Fmoc solid-phase synthesis method to obtain the crude ACTH (human sequence) or analogue peptidyl-resin with protective groups, wherein the reaction temperature of C-15 peptide synthesis is 40-60° C. After cleavge and precipitation, the crude product of ACTH (human sequence) or analogue is obtained, and then the high-purity product is obtained by liquid chromatography. The chromatographic purity of ACTH (human sequence) or analogue prepared by the invention is more than 99%, the stability is good, and the yield of the target peptide is ≥63%.

19 Claims, 14 Drawing Sheets
Specification includes a Sequence Listing.

| No. | Retention Time min | Area mAu*min | Height mAu | Relative Area % | Relative Height % |
|---|---|---|---|---|---|
| 1 | 8.902 | 4.749 | 41.854 | 2.28 | 4.71 |
| 2 | 9.709 | 11.969 | 90.687 | 5.74 | 10.22 |
| 3 | 9.922 | 2.323 | 13.451 | 1.11 | 1.52 |
| 4 | 10.402 | 0.682 | 2.287 | 0.33 | 0.26 |
| 5 | 11.456 | 0.773 | 2.025 | 0.37 | 0.23 |
| 6 | 15.076 | 1.660 | 5.270 | 0.80 | 0.59 |
| 7 | 17.776 | 0.609 | 1.692 | 0.29 | 0.19 |
| 8 | 18.882 | 1.515 | 3.482 | 0.73 | 0.39 |
| 9 | 19.896 | 148.271 | 561.259 | 71.06 | 63.23 |
| 10 | 20.996 | 1.936 | 7.334 | 0.93 | 0.83 |
| 11 | 21.269 | 1.388 | 5.099 | 0.67 | 0.57 |
| 12 | 22.009 | 0.735 | 2.763 | 0.35 | 0.31 |
| 13 | 22.542 | 2.391 | 4.806 | 1.15 | 0.54 |
| 14 | 24.136 | 5.283 | 11.076 | 2.53 | 1.25 |
| 15 | 25.609 | 0.786 | 1.402 | 0.38 | 0.16 |
| 16 | 27.762 | 4.395 | 14.178 | 2.11 | 1.60 |
| 17 | 29.236 | 0.628 | 2.558 | 0.30 | 0.29 |
| 18 | 29.856 | 1.113 | 4.200 | 0.53 | 0.47 |
| 19 | 30.436 | 0.760 | 5.137 | 0.36 | 0.58 |
| 20 | 30.722 | 6.591 | 41.630 | 3.16 | 4.69 |
| 21 | 30.849 | 5.518 | 32.477 | 2.64 | 3.66 |
| 22 | 31.176 | 1.500 | 9.486 | 0.72 | 1.07 |
| 23 | 31.462 | 1.308 | 8.972 | 0.63 | 1.01 |
| 24 | 32.769 | 1.778 | 14.581 | 0.85 | 1.64 |
| Total | | 208.662 | 887.707 | 100.00 | 100.00 |

| No. | Retention Time min | Area mAU*min | Height mAu | Relative Area % | Relative Height % |
|---|---|---|---|---|---|
| 1 | 3.433 | 0.500 | 3.158 | 0.20 | 0.28 |
| 2 | 9.075 | 0.498 | 3.495 | 0.20 | 0.31 |
| 3 | 9.248 | 0.204 | 1.739 | 0.08 | 0.16 |
| 4 | 9.688 | 2.909 | 23.419 | 1.18 | 2.11 |
| 5 | 9.981 | 2.677 | 18.085 | 1.08 | 1.63 |
| 6 | 10.241 | 0.568 | 3.691 | 0.23 | 0.33 |
| 7 | 10.461 | 0.262 | 1.866 | 0.11 | 0.17 |
| 8 | 10.661 | 0.374 | 1.569 | 0.15 | 0.14 |
| 9 | 11.608 | 0.314 | 1.567 | 0.13 | 0.14 |
| 10 | 11.978 | 0.193 | 0.910 | 0.08 | 0.08 |
| 11 | 12.748 | 0.587 | 2.097 | 0.24 | 0.19 |
| 12 | 13.175 | 0.258 | 0.898 | 0.10 | 0.08 |
| 13 | 14.141 | 0.399 | 0.763 | 0.16 | 0.07 |
| 14 | 15.128 | 1.063 | 4.535 | 0.43 | 0.41 |
| 15 | 16.315 | 1.159 | 5.800 | 0.47 | 0.52 |
| 16 | 18.015 | 0.664 | 1.595 | 0.27 | 0.14 |
| 17 | 18.475 | 0.200 | 0.801 | 0.08 | 0.07 |
| 18 | 19.181 | 1.980 | 4.325 | 0.80 | 0.39 |
| 19 | 20.195 | 168.214 | 697.385 | 68.00 | 62.85 |
| 20 | 21.333 | 2.774 | 9.824 | 1.12 | 0.89 |
| 21 | 21.655 | 2.019 | 6.763 | 0.82 | 0.61 |
| 22 | 22.375 | 2.395 | 9.127 | 0.97 | 0.82 |
| 23 | 22.978 | 4.118 | 9.640 | 1.66 | 0.87 |
| 24 | 23.735 | 0.288 | 1.258 | 0.12 | 0.11 |
| 25 | 24.201 | 0.284 | 1.527 | 0.11 | 0.14 |
| 26 | 24.688 | 7.338 | 18.316 | 2.97 | 1.65 |
| 27 | 25.378 | 0.446 | 1.567 | 0.18 | 0.14 |
| 28 | 26.108 | 1.251 | 3.611 | 0.51 | 0.33 |
| 29 | 27.375 | 0.233 | 0.853 | 0.10 | 0.08 |
| 30 | 27.781 | 0.212 | 0.985 | 0.09 | 0.09 |
| 31 | 28.308 | 6.757 | 23.782 | 2.73 | 2.14 |
| 32 | 29.568 | 1.591 | 7.811 | 0.64 | 0.70 |
| 33 | 30.181 | 3.044 | 14.163 | 1.23 | 1.28 |
| 34 | 30.621 | 2.637 | 17.480 | 1.07 | 1.58 |
| 35 | 30.888 | 8.480 | 38.984 | 3.43 | 3.53 |
| 36 | 30.973 | 5.833 | 41.999 | 2.38 | 3.79 |
| 37 | 31.335 | 3.613 | 21.876 | 1.46 | 1.97 |
| 38 | 31.595 | 3.933 | 25.293 | 1.59 | 2.34 |
| 39 | 31.835 | 1.267 | 6.475 | 0.51 | 0.58 |
| 40 | 32.093 | 0.373 | 2.872 | 0.15 | 0.26 |
| 41 | 32.248 | 0.544 | 2.686 | 0.22 | 0.24 |
| 42 | 32.535 | 0.221 | 1.816 | 0.09 | 0.16 |
| 43 | 32.688 | 0.203 | 1.568 | 0.08 | 0.14 |
| 44 | 33.888 | 4.674 | 38.842 | 1.89 | 3.50 |
| Total | | 247.374 | 1109.571 | 100.00 | 100.00 |

# HIGH-PURITY ADRENOCORTICOTROPIC HORMONE, ANALOGUE AND A LARGE-SCALE PREPARATION METHOD THEREOF

CROSS-REFERENCE TO RELATED APPLICATIONS

This application is a continuation application of International PCT Application No. PCT/CN2021/086395, filed on Apr. 12, 2021. The entirety of each of the abovementioned patent applications is herein incorporated by reference and made a part of this specification.

REFERENCE TO SEQUENCE LISTING

The instant application contains a Sequence Listing which has been submitted electronically in ASCII format and is hereby incorporated by reference in its entirety. Said ASCII copy, created on Jul. 8, 2021, is named Seq_Listing_132298_00102.txt and is 38,702 bytes in size.

BACKGROUND

Technical Field

The invention relates to the technical field of peptide solid-phase synthesis and purification preparation method, in particular to a high-purity adrenocorticotropic hormone (ACTH) (human sequence) or ACTH analogue and a large-scale preparation method thereof.

Description of Related Art

Adrenocorticotropic hormone (corticotropin, ACTH for short) is a polypeptide hormone produced and secreted by the pituitary gland, comprising 39 amino acid residues coupled in a linear sequence. The N-terminal 24-amino acid segment is identical in all species and contains the adrenocorticotrophic activity. ACTH stimulates the cortex of the adrenal gland and boosts the synthesis of corticosteroids, mainly glucocorticoids but also sex steroids. It is used in the treatment of certain neurological diseases such as infantile spasm and multiple sclerosis, and diagnostically to investigate adrenocortical insufficiency. It has a role as a diagnostic reagent. It is a polypeptide, a peptide hormone and a biomacromolecule.

Infantile spasm is an age-related epilepsy syndrome accompanied by retrogression phenomenon of mental and motor development. For a long time, ACTH extracted from animals has been used as the first-line drug for the treatment of infantile spasm, but its mechanism of action is unclear.

The ACTH drug products currently on the market, whose ACTH raw materials are all extracted from animals, have the risk of immunogenicity and are prone to adverse reactions, while the ACTH manufactured by chemical synthesis can reduce the risk of immunogenicity. However, adrenocorticotropic hormone of human sequence has not been developed into drug products in the prior art.

The sequence of ACTH (porcine sequence) on the market is SEQ ID NO: 1 and/or SEQ ID NO: 2:

(SEQ ID NO: 1)
$NH_2$-$Ser^1$-$Tyr^2$-$Ser^3$-$Met^4$-$Glu^5$-$His^6$-$Phe^7$-$Arg^8$-$Trp^9$-

$Gly^{10}$-$Lys^{11}$-$Pro^{12}$-$Val^{13}$-$Gly^{14}$-$Lys^{15}$-$Lys^{16}$-$Arg^{17}$-$Arg^{18}$-

-continued $Pro^{19}$-$Val^{20}$-$Lys^{21}$-$Val^{22}$-$Tyr^{23}$-$Pro^{24}$-$Asn^{25}$-$Gly^{26}$-$Ala^{27}$-

$Glu^{28}$-$Asp^{29}$-$Glu^{30}$-$Leu^{31}$-$Ala^{32}$-$Glu^{33}$-$Ala^{34}$-$Phe^{35}$-$Pro^{36}$-

$Leu^{37}$-$Glu^{38}$-$Phe^{39}$-COOH.

(SEQ ID NO: 2)
$NH_2$-$Ser^1$-$Tyr^2$-$Ser^3$-$Met^4$-$Glu^5$-$His^6$-$Phe^7$-$Arg^8$-$Trp^9$-

$Gly^{10}$-$Lys^{11}$-$Pro^{12}$-$Val^{13}$-$Gly^{14}$-$Lys^{15}$-$Lys^{16}$-$Arg^{17}$-$Arg^{18}$-

$Pro^{19}$-$Val^{20}$-$Lys^{21}$-$Val^{22}$-$Tyr^{23}$-$Pro^{24}$-$Asp^{25}$-$Gly^{26}$-$Ala^{27}$-

$Glu^{28}$-$Asp^{29}$-$Glu^{30}$-$Leu^{31}$-$Ala^{32}$-$Glu^{33}$-$Ala^{34}$-$Phe^{35}$-$Pro^{36}$-

$Leu^{37}$-$Glu^{38}$-$Phe^{39}$-COOH.

In the above-mentioned SEQ ID NO: 1, the N-25 Asn is unstable under alkaline conditions, and can be transformed into Asp by deamination, usually, the porcine ACTH (SEQ ID NO: 1) extracted from the pig pituitary gland contains part of N-25 deamidated ACTH (SEQ ID NO: 2).

The sequence of ACTH (human sequence) is as follows:

(SEQ ID NO: 3)
$NH_2$-$Ser^1$-$Tyr^2$-$Ser^3$-$Met^4$-$Glu^5$-$His^6$-$Phe^7$-$Arg^8$-$Trp^9$-

$Gly^{10}$-$Lys^{11}$-$Pro^{12}$-$Val^{13}$-$Gly^{14}$-$Lys^{15}$-$Lys^{16}$-$Arg^{17}$-

$Arg^{18}$-$Pro^{19}$-$Val^{20}$-$Lys^{21}$-$Val^{22}$-$Tyr^{23}$-$Pro^{24}$-$Asn^{25}$-

$Gly^{26}$-$Ala^{27}$-$Glu^{28}$-$Asp^{29}$-$Glu^{30}$-$Ser^{31}$-$Ala^{32}$-$Glu_{33}$-

$Ala_{34}$-$Phe_{35}$-$Pro_{36}$-$Leu_{37}$-$Glu_{38}$-$Phe_{39}$-COOH, the amino acids are abbreviated as

SYSMEHFRWGKPVGKKRRPVKVYPNGAEDESAEAFPLEF.

The sequence of N-25 deamidated ACTH (human sequence) or ACTH (human sequence) analogue is as follows:

(SEQ ID NO: 4)
$NH_2$-$Ser^1$-$Tyr^2$-$Ser^3$-$Met^4$-$Glu^5$-$His^6$-$Phe^7$-$Arg^8$-$Trp^9$-

$Gly^{10}$-$Lys^{11}$-$Pro^{12}$-$Val^{13}$-$Gly^{14}$-$Lys^{15}$-$Lys^{16}$-$Arg^{17}$-$Arg^{18}$-

$Pro^{19}$-$Val^{20}$-$Lys^{21}$-$Val^{22}$-$Tyr^{23}$-$Pro^{24}$-$Asp^{25}$-$Gly^{26}$-$Ala^{27}$-

$Glu^{28}$-$Asp^{29}$-$Glu^{30}$-$Ser^{31}$-$Ala^{32}$-$Glu^{33}$-$Ala^{34}$-$Phe^{35}$-$Pro^{36}$-

$Leu^{37}$-$Glu^{38}$-$Phe^{39}$-COOH, the amino acids are abbreviated as

SYSMEHFRWGKPVGKKRRPVKVYPDGAEDESAEAFPLEF.

In the above-mentioned SEQ ID NO: 3, as the N-25 Asn is unstable under alkaline conditions, which can be transformed into Asp by deamination, so part of ACTH (human sequence) (SEQ ID NO: 3) may be transformed into the form of N-25 deamidated ACTH (human sequence) (SEQ ID NO: 4). In the invention, when SEQ ID NO: 3 is prepared by the solid-phase synthesis, less than 1% of the related peptide as SEQ ID NO: 4 may generated by deamination reaction. The prior art discloses that the Asp-Gly-containing sequences are more likely to occur aspartimide formation when Gly located at the C-terminus of the aspartic acid. Val-Tyr-Pro-Asn-Gly-Ala, a fragment of ACTH, is more prone to deamidation reaction at pH 5-12. ACTH also exists in two forms in vivo (H. Tonie Wright. Nonenzymatic Deamidation of Asparaginyl and Glutaminyl Residues in Proteins. Critical reviews in Biochemistry and Molecular Biology, 1991, 26(1):1-52).

Therefore, ACTH (human sequence) or analogue thereof and commercial porcine ACTH sequence differ mainly in the N-31 amino acid.

In the prior art, the Boc solid-phase synthesis technology is adopted in example 1-6 of U.S. Pat. No. 4,055,524, the protected amino acid used in the Boc solid-phase synthesis technique and the Fmoc solid-phase synthesis technique are different, and the following disadvantages exist in Boc solid-phase synthesis technology. Acid is repeatedly used to deprotect during the synthesis process, for example trifluoroacetic acid is used to deprotect BOC and other protection groups, resulting that some peptides will fall off from the resin. The longer the synthetic peptide chain, the more serious the loss. Acid treatment can also cause some side reactions of the side chain. BOC solid-phase synthesis is especially unsuitable for the synthesis of peptides containing tryptophan which is unstable to acids. Hydrofluoric acid is adopted in the final deprotection reaction, which is extremely corrosive and highly toxic, and there are big challenges in industrial production.

A liquid-phase method (not solid-phase synthesis technology, all steps 1-14 are carried out by liquid-phase reaction in solution system, and intermediates achieved in steps needed to be separated and purified by crystallization or even column chromatography to remove redundant unreacted reactant and reagents) is disclosed in example 4 steps 1-14 of U.S. Pat. No. 3,953,415 for preparing ACTH (human sequence), and the crude peptide with protective group was synthesized by liquid-phase method, the trifluoroacetic acid was used for deprotection, salt type of the residue was transferred by ion exchange and the crude produc is obtained after lyophilizationt. The crude product was purified by ion exchange and eluted with ammonium acetate solution during the purification process. Ammonium acetate was not removed from the product after freeze-drying. The total molar yield of the process was only 17% (89.9% in step 1, 99% in step 2, 97.2% in step 3, 92.7% in step 4, 93% in step 5, 95% in step 6, 86.2% in step 7, 82.6% in step 8, 96.9% in step 9, 88% in step 10, 86.1% in step 11, 90% in step 12, 85% in step 13 and 60% in step 14), the yield was low, and the specific purity was unclear.

Kálmán et al. reported that the crude peptide with protective group was synthesized by liquid-phase method. (Synthesis of Human ACTH and Its Biologically Active Fragments [M]. The Chemistry of Polypeptides. Springer US, 1973.) The purification process was not provided, and the specific purity and yield were unclear.

In the prior art, the preparation of ACTH (human sequence) adopts Boc solid-phase synthesis technology or liquid-phase fragment synthesis method. There are many problems such as low yield, low purity, many kinds of impurities and difficult post-treatment and so on due to incomplete reaction. Therefore, it is urgent to develop a high-purity ACTH (human sequence) or ACTH analogue and preparation method thereof which can effectively overcome the above defects.

SUMMARY

In view of the shortcomings of the prior art, the invention provides a high-purity ACTH (human sequence) or ACTH analogue and preparation method thereof. The method adopts Fmoc solid-phase synthesis technology to obtain the product, the synthesis conditions of C-15 peptide and post-treatment conditions are optimized to solve the problems such as reaction incompletely, many deletion peptide impurities and difficult in purification.

In the present invention, the relevant nouns or abbreviations are explained in the following table:

| Abbreviation | Meaning |
| --- | --- |
| Boc | T-butoxycarbonyl |
| Cbz | Benzyloxycarbonyl |
| DCM | Dichloromethane |
| DIC | N,N'-diisopropylcarbodiimide |
| DIEA | N,N-diisopropylethylamine |
| DIPEA | N,N-diisopropylethylamine |
| DMF | N,N-dimethylformamide |
| Fmoc | 9-fluorene methoxycarbonyl |
| HOBt | 1-hydroxybenzotriazole |
| HBTU | Benzotriazole-N,N,N',N'-tetramethylurea hexafluorophosphate |
| NMP | N-methylpyrrolidone |
| OtBu | O-tertiary butyl |
| Oxyma Pure | Ethyl cyanoglyoxylate-2-oxime |
| Pbf | 2,2,4,6,7-pentamethyldihydrobenzofuran-5-sulfonyl |
| PyBop | Benzotriazol-1-yl-oxytripyrrolidinophosphonium hexafluorophosphate |
| PS | Polystyrene |
| TBTU | O-(Benzotriazol-1-yl)-N,N,N',N'-tetramethyluronium tetrafluoroborate |
| tBu | Tert-butyl group |
| Tris | Tris(hydroxymethyl)methyl aminomethane |
| Trt | Triphenylmethyl |

Unless otherwise specified, the interpretation of relevant nouns involved in the present invention adopts the conventional interpretation of the prior art.

In order to achieve the above purpose, the invention provides the following technical solution, a composition containing ACTH (human sequence), wherein the purity of the ACTH (human sequence) is ≥99%, the content of the maximum single impurity is ≤0.5%, and the content of the total impurities is ≤1%, and the sequence of the ACTH from the N-terminal to the C-terminal is as follows:

(SEQ ID NO: 3)
SYSMEHFRWGKPVGKKRRPVKVYPNGAEDESAEAFPLEF.

In order to achieve the above purpose, the invention provides another technical solution as follows: a composition containing ACTH analogue, wherein the purity of the ACTH analogue is ≥99%, the content of the maximum single impurity is ≤0.5%, and the content of the total impurities is ≤1%. The sequence of the ACTH analogue from the N-terminal to the C-terminal is as follows:

(SEQ ID NO: 4)
SYSMEHFRWGKPVGKKRRPVKVYPDGAEDESAEAFPLEF.

The purity is preferably determined by high performance liquid chromatography (HPLC). The purity of the high-purity ACTH (human sequence) or analogue thereof is at least 99.0%, or at least 99.5%, or at least 99.8%, or higher. The content of the maximum single impurity of the high-purity ACTH (human sequence) or analogue thereof is ≤0.5%, and the content of the total impurities is ≤1. Preferably, the content of the maximum single impurity is ≤0.4% and the content of the total impurities is ≤0.9%. Preferably, the content of the maximum single impurity is ≤0.3% and the content of the total impurities is ≤0.8%. Preferably, the content of the maximum single impurity is ≤0.2% and the content of the total impurities is ≤0.7%. Preferably, the content of the maximum single impurity is ≤0.1% and the content of the total impurities is ≤0.5% or less.

As a further preference of the invention, the purity of the ACTH or ACTH analogue is ≥99.5%, the content of the maximum single impurity is ≤0.1%, and the content of the total impurities is ≤0.5%.

The composition containing ACTH or analogue thereof (purity ≥99%, HPLC) is obtained by the following preparation method: the amino acids are coupled from the C-terminal to the N-terminal according to the amino acid sequence shown in SEQ ID NO: 3 or SEQ ID NO: 4 by Fmoc solid-phase synthesis method, and then purified to obtain the composition containing ACTH or analogue thereof. As a further preference of the invention, the preparation method of the high-purity ACTH (human sequence) or analogue thereof comprises the following steps:

1) Through Fmoc solid-phase synthesis method, amino acids are coupled from the C-terminal to the N-terminal according to the amino acid sequence shown in SEQ ID NO: 3 or SEQ ID NO: 4 to obtain the peptidyl-resin of ACTH or analogue thereof with protective groups;

2) Treatment of the peptidyl-resin of ACTH or analogue thereof with protective groups by cleavage cocktail, a solution containing ACTH or analogue thereof is obtained after cleaving ACTH or analogue thereof from the resin and removing all the protective groups from the peptide chain;

3) The solution containing ACTH or analogue thereof is treated with precipitation reagent to obtain crude product of ACTH or analogue thereof;

4) The crude product of the ACTH or analogue thereof is purified by liquid chromatography to obtain a composition containing the ACTH or analogue thereof.

In the technical solution of the invention, the Fmoc solid-phase synthesis method refers to a synthesis method that connects reactants to an insoluble solid-phase carrier. The principle of Fmoc solid-phase synthesis is that, firstly chloromethyl ($-CH_2Cl$) or other groups that can react with carboxyl groups are attached to an insoluble support (such as resin), after this functional group reacts with an amino acid whose amino group is protected, the first amino acid is immobilized on the resin, then the amino acid monomers are attached to the resin in sequence according to the design sequence to obtain the target peptide of the desired polypeptide sequence. During the synthesis process, the polypeptide is stably covalent bound to the surface of the solid carrier, After the reaction, the peptide is cleaved from the solid carrier by special chemical reagent. The Fmoc solid-phase synthesis method can simplify the reaction procedure and the post-treatment process, reduce the difficulty of purification steps and reduce the loss of the product in the post-treatment stage. However, in the traditional liquid-phase synthesis method, the residual raw materials, reagents in the target intermediates or products need to be separated and purified by crystallization or even column chromatography. The traditional liquid phase synthesis has the disadvantages of complicated operation, long production cycle and heavy workload. In addition, the length of the peptides that can be synthesized by the liquid phase synthesis method is relatively short, and the sequence length is usually within 10 amino acids.

In the technical solution of the invention, the cleavage cocktail refers to the chemical reagent that can cleave the synthesized polypeptide from the solid carrier and remove the protection of side chain.

In the technical solution of the invention, the precipitation reagent refers to the chemical reagent that can precipitate the synthesized polypeptide from the cleavage cocktail solution.

In the technical solution of the invention, in step 1), the amino acids are coupled stepwise or fragment, and the N-terminal of each amino acid is protected by Fmoc group.

In the technical solution of the invention, in step 1), the solid-phase synthetic resin can be selected from Chloromethyl resin or Wang resin (polybenzyloxy benzyl alcohol resin) or 2-triphenylmethylchloromethane resin or Rink Amide AM Resin or Rink Amide MBHA Resin or Rink Amide Resin and so on, preferably 2-triphenylmethylchloromethane resin. The degree of substitution of resin is 0.1-1.0 mmol/g, preferably 0.2-0.8 mmol/g.

In the technical solution of the invention, in step 1), anchoring of the first residue Fmoc-Phe-OH to the synthesis support can be selected as follows: the solid-phase synthetic resin is swelled with 6-20 L/Kg resin organic solvent such as DCM, then Fmoc-Phe-OH and organic amine such as DIPEA are added and the reaction is conducted at room temperature for 2-4 h to obtain Fmoc-Phe-resin. Then DIPEA/methanol (the volume ratio is 1:5-1:15) is added to cap the unreacted site, finally, the resin is washed with 6-20 L/Kg resin organic solvents such as DCM, DMF, NMP or methanol. After filtration and drying under vacuum, the Fmoc-Phe-resin is obtained for subsequent use. Fmoc-Phe-resin is taken to measure the substitution to determine the feeding amount. In the technical solution of the invention, Fmoc-Phe-OH can also be directly purchased from commercial vendor without preparing by oneself.

In the technical solution of the invention, in step 1), the method for coupling amino acids AA except Fmoc-Phe-OH is as follows:

i. The Fmoc-$AA_n$-resin was swelled by a first organic solvent, wherein $AA_n$ means that n amino acids have been connected to the resin, and n is a natural number from 1 to 38. Alternatively, the structure of the amino acid AA is the same or different, the N-terminal of amino acid AA is protected by Fmoc or Boc or Cbz group, and the side-chain of amino acid AA is protected by groups or not;

ii. The Fmoc-$AA_n$-resin is deprotected with a second organic solvent until the Fmoc protecting group is completely removed, and finally H-$AA_n$-resin is obtained by washing with a third organic solvent;

iii. Fmoc-$AA_m$OH is reacted with activation reagent in the first organic solvent to obtain solution containing the activated Fmoc-$AA_m$OH derivative solution, wherein m means the (n+1)th amino acid. Alternatively, step iii) may be completed before or after step i) or step ii);

iv. The activated Fmoc-$AA_m$OH derivative solution is mixed with H-$AA_n$-resin and Fmoc-$AA_{(n+1)}$resin is obtained after the coupling reaction, then the Fmoc-$AA_{(n+1)}$-resin is washed with the third organic solvent;

v. Recycle the method of step ii) to step iv) to connect the remaining amino acid residues to the Fmoc-$AA_{(n+1)}$-resin after washing as described above is to obtain the ACTH or analogue thereof peptidyl-resin with side-chain protective groups.

In the technical solution of the invention, the first organic solvent in the step i) and iii) is an aprotic solvent, preferably one or more of DCM, DMF, NMP, or the mixed solution of any one of them with HOBt, preferably the mixed solution of any one or more of DCM, DMF, NMP with 0.1-10% HOBt (mass/volume); preferably, one of the DCM solution containing 1% HOBt (mass/volume), DMF solution containing 1% HOBt (mass/volume), or NMP solution containing 1% HOBt (mass/volume) calculated by mass volume ratio. Because HOBt in appropriate amount can inhibit the racemization of amino acids in coupling reaction, and the DMF solution containing 1% HOBt is the most preferred solution (mass/volume). The volume mass ratio of the first organic solvent to Fmoc-Phe-resin is 6-20 L: 1 Kg.

In the technical solution of the invention, the second organic solvent in step ii) is an aprotic solvent containing an organic base selected from one or more of piperidine, piperazine, diethylamine or triethylamine, preferably one of DCM solution containing 15-30% piperidine (volume ratio), DMF solution containing 15-30% piperidine (volume ratio) or NMP solution containing 15-30% piperidine (volume ratio) calculated by volume ratio, further preferably one of DCM solution containing 20% piperidine (volume ratio), DMF solution containing 20% piperidine (volume ratio) and NMP solution containing 20% piperidine (volume ratio). The most preferred solution is DMF solution containing 20% piperidine. The volume mass ratio of deprotection reagent to Fmoc-Phe-resin is 6-20 L/Kg. The reaction time of deprotection reaction is 1-30 min, then the H-AA$_n$-resin is drained, and the deprotection reaction is repeated for 1-5 times until the Fmoc is completely removed.

In the technical solution of the invention, the third organic solvent in step ii) is the first organic solvent or alcohol solvent, and the third organic solvent is one or more of DCM, methanol, ethanol, DMF, NMP, or the mixed solution of any one of them with HOBt; preferably the mixed solution of any one or more of DCM, methanol, ethanol, DMF and NMP with 0.1-10% HOBt (mass/volume); preferably, one or more of DCM solution containing 1% HOBt, DMF solution containing 1% HOBt and NMP solution containing 1% HOBt. The most preference is DMF solution. The volume mass ratio of the third organic solvent to the Fmoc-Phe-resin is 6-20 L: 1 Kg. The third organic solvent is used for washing for 4-10 times, preferably 6-9 times and even preferably 8 times. The third organic solvent for the last washing shall not be the solvent that can shrink the resin.

In the technical solution of the invention, the activation reagent in step iii) is one of the composition of DIC, HBTU and Oxyma Pure, composition of DIC and Oxyma Pure, composition of DIC and HOBt, composition of DIEA, TBTU and HOBt, and composition of DIEA and PyBop. Preferably, the coupling agent is the composition of DIC and Oxyma Pure, because the composition can better inhibit the racemization in the coupling reaction and drive the acylation to completion. The amount of each coupling reagent is 3-10 molar equivalents, preferably 5 molar equivalents. The temperature of the activation is room temperature and the activation time is 5-60 min.

In the technical solution of the invention, in step iv, the reaction temperature for coupling is 10-35° C. and the reaction time is 0.5-5 h besides the coupling at C-15 position. After deprotection, the peptidyl-resin is drained and then washed with the third organic solvent for 4-10 times. The third organic solvent for the last washing shall not be the solvent that can shrink the resin.

In the technical solution of the invention, the method of Ninhydrin Test is applied for monitoring the coupling reaction process. The specific detection method is referred to a literature "a more practical quantitative determination method of amino acids—Ninhydrin method". If the test result is negative, the next reaction is conducted. If the test result is positive, repeat the coupling reaction until the test result is negative.

In the technical solution of the invention, when coupling the amino acid at position C-15, the temperature of the coupling reaction in step iv) is about 40-60° C., most preferably about 45-55° C., such as about 40° C., about 42° C., about 45° C., about 48° C., about 50° C., about 52° C., about 55° C., about 58° C., about 60° C., etc. If there is no special description, the "about" in the invention refers to appropriately close to the said value, such as adding or subtracting 10%. Urea or perchlorate can be added into the coupling reaction mixture. As a further improvement of the invention, urea of about 0.1-1 Kg/Kg Fmoc-Phe-resin or perchlorate of about 0.1-1 Kg/Kg Fmoc-Phe-resin can be added, that is, the mass ratio of the urea or perchlorate to Fmoc-Phe-resin is about 0.1:1-1:1. The reaction time of coupling C-15 peptide is about 0.5-16 h, preferably about 2-4 h. It is found that under the condition of 10-30° C., using various coupling reagents (such as combination of DIC/HOBt, combination of TBTU/DIPEA, combination of TBTU/DIPEA/HOBt, combination of Oxyma Pure/PyBop/DIPEA, combination of DIC/HOBt/urea, combination of DIC/HOBt/NaClO$_4$), even adding urea and sodium perchlorate to disrupt β sheets, the detection results of Ninhydrin test are still positive. The problem of difficult condensation could not be solved even if the coupling is repeated and the coupling reaction time is prolonged. In general, increasing the temperature of the reaction may improve the coupling rate, but it may promote the formation of undesired byproducts D-isomer impurities at the same time. It is surprisingly found that the coupling rate is significantly improved by increasing the reaction temperature to 40-60° C. and adding urea or sodium perchlorate optionally, and the formation of D-isomer impurity is not observed or is at a very low level at about 60° C. at the same time.

In the technical solution of the invention, the peptidyl-resin of ACTH (human sequence) or analogue thereof with protective group obtained in step 1) is deprotected with the second organic solvent, then washed with the third organic solvent, and finally washed with the fourth organic solvent, which the fourth organic solvent is one or more of methanol, ethanol and DCM, preferably methanol.

In the technical solution of the invention, the cleavage cocktail is composed of trifluoroacetic acid and scavengers in step 2). The scavengers is composed of one or more of phenol, benzyl sulfide, dimethyl sulfide, 1,2-ethanedithiol, triethylsilane, triisopropylsilane or water. The probability of amino acids being modified or oxidized can be reduced by adding the scavengers. The volume ratio of scavengers to trifluoroacetic acid is 1:4-1:19, for example, the concentration of trifluoroacetic acid is 80%-95%, preferably 90%. The total concentration of scavengers is 5%-20%, preferably 10%.

In the technical solution of the invention, in step 3), the precipitation reagent is =ether solvent, referably ether or methyl tert-butyl ether, even preferably methyl ter-tbutyl ether.

In the technical solution of the invention, the volume ratio of the cleavage cocktail to the precipitation reagent in step 3) is 1:5-1:20.

In the technical solution of the invention, the liquid chromatography method in step 4) is reversed-phase high-pressure liquid chromatography, and the stationary phase for purification is octylsilane chemically bonded silica, octadecylsilane chemically bonded silica or PS reversed-phase polymer chromatographic packing, and the dynamic axial compression column is used, 0.01-0.2 mol/L organic salt solution and organic solvent or inorganic salt solution and organic solvent as mobile phase is used for purification. The combination of alkaline and acidic conditions is used for purification, The preferred mobile phases are 0.1 mol/L Tris aqueous solution/acetonitrile in alkaline condition is used firstly and then 0.1 mol/L acidic ammonium sulfate aqueous solution/acetonitrile in acidic condition.

In the technical solution of the invention, desalting is required after purification in step 4). In the desalting process, 0.01-0.2 mol/L ammonium acetate aqueous solution/acetonitrile is used as the mobile phase for desalting, and then 20-80% acetonitrile aqueous solution with a mass concentration of 0.01-0.2% acetic acid is used to elute the sample.

In the technical solution of the invention, the following peptidyl-resin is adopted, which has the following sequence: Q-P-resin, the P is Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe (SEQ ID NO: 5), the resin is 2-triphenylmethylchloromethane resin, and the Q is absent or is selected from one or more of the following combination:

H-Pro-,

H-Tyr(tBu)-Pro-,

H-Val-Tyr(tBu)-Pro-,

H-Lys(Boc)-Val-Tyr(tBu)-Pro-,

H-Val-Lys(Boc)-Val-Tyr(tBu)-Pro-,

H-Pro-Val-Lys(Boc)-Val-Tyr(tBu)-Pro-,

H-Arg(Pbf)-Pro-Val-Lys(Boc)-Val-Tyr(tBu)-Pro-,

H-Arg(Pbf)-Arg(Pbf)-Pro-Val-Lys(Boc)-Val-Tyr(tBu)-Pro-,

H-Lys(Boc)-Arg(Pbf)-Arg(Pbf)-Pro-Val-Lys(Boc)-Val-Tyr(tBu)-Pro-,

H-Lys(Boc)-Lys(Boc)-Arg(Pbf)-Arg(Pbf)-Pro-Val-Lys(Boc)-Val-Tyr(tBu)-Pro-,

H-Gly-Lys(Boc)-Lys(Boc)-Arg(Pbf)-Arg(Pbf)-Pro-Val-Lys(Boc)-Val-Tyr(tBu)-Pro-,

H-Val-Gly-Lys(Boc)-Lys(Boc)-Arg(Pbf)-Arg(Pbf)-Pro-Val-Lys(Boc)-Val-Tyr(tBu)-Pro-,

H-Pro-Val-Gly-Lys(Boc)-Lys(Boc)-Arg(Pbf)-Arg(Pbf)-Pro-Val-Lys(Boc)-Val-Tyr(tBu)-Pro-,

H-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-,

H-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-,

H-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-,

H-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-,

H-Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-,

H-His(Trt)-Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-,

H-Glu(OtBu)-His(Trt)-Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-,

H-Met-Glu(OtBu)-His(Trt)-Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-,

H-Ser(tBu)-Met-Glu(OtBu)-His(Trt)-Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-,

H-Tyr(tBu)-Ser(tBu)-Met-Glu(OtBu)-His(Trt)-Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-,

H-Ser(tBu)-Tyr(tBu)-Ser(tBu)-Met-Glu(OtBu)-His(Trt)-Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-.

The peptidyl-resin of the invention, wherein the peptide has the following sequence selected from SEQ ID NO: 6~SEQ ID NO: 29:

(SEQ ID NO: 6)
Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 7)
Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 8)
Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 9)
Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 10)
Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 11)
Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 12)
Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 13)
Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 14)
Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 15)
Lys(Boc)-Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 16)
Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 17)
Val-Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 18)
Pro-Val-Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 19)
Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 20)
Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 21)
Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 22)
Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 23)
Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 24)
His(Trt)-Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

-continued (SEQ ID NO: 25)
Glu(OtBu)-His(Trt)-Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 26)
Met-Glu(OtBu)-His(Trt)-Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 27)
Ser(tBu)-Met-Glu(OtBu)-His(Trt)-Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 28)
Tyr(tBu)-Ser(tBu)-Met-Glu(OtBu)-His(Trt)-Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe;

(SEQ ID NO: 29)
Ser(tBu)-Tyr(tBu)-Ser(tBu)-Met-Glu(OtBu)-His(Trt)-Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe.

The Fmoc solid-phase synthesis process described in the invention is not only suitable for small-scale laboratory synthesis, but also suitable for various pilot and large-scale manufacture, such as large-scale single batch production of high-purity ACTH (human sequence) with an output of at least about 250 g/batch, or at least about 300 g/batch, or at least about 500 g/batch, or even kilogram scale. It shows that the solid phase synthesis process has good stability and is suitable for commercial production. The "single batch" of the invention refers to a specified amount of product synthesized at one time. Therefore, a single batch does not include multiple productions at separate times or in separate amounts and then combined.

The high-purity ACTH (human sequence) or analogue thereof can form a composition alone or with other pharmaceutical excipients or other active components, which can be used to prepare formulation products, such as oral dosage form, parenteral dosage form, rectal dosage form or topical dosage form and other suitable dosage forms for ACTH (human sequence) or analogue thereof. The oral dosage forms include but are not limited to tablets, capsules, granules, pills, powders, sustained and controlled release preparations. The parenteral dosage forms include but are not limited to sterile solutions, suspensions or emulsions. Rectal dosage forms include but are not limited to suppositories. The topical dosage forms include but are not limited to inhaling agents, patches, ointments, etc.

As a further preference of the invention, the invention relates to a pharmaceutical composition comprising ACTH (human sequence) and medicinal carrier, wherein the purity of the ACTH is ≥99%, the content of any single impurity is ≤0.5%, and the content of the total impurities is ≤1%, and the sequence of the ACTH from the N-terminal to the C-terminal is as follows:

(SEQ ID NO: 3)
SYSMEHFRWGKPVGKKRRPVKVYPNGAEDESAEAFPLEF.

As a further preference of the invention, the invention relates to a pharmaceutical composition comprising ACTH analogue and medicinal carrier, wherein the purity of the ACTH analogue is ≥99%, the content of any single impurity is ≤0.5%, and the content of the total impurity is ≤1%, and the sequence of the ACTH analogue from the N-terminal to the C-terminal is as follows:

(SEQ ID NO: 4)
SYSMEHFRWGKPVGKKRRPVKVYPDGAEDESAEAFPLEF.

The ACTH (human sequence) or ACTH analogue and related formulation products with high purity can be used for treating infantile spasms, multiple sclerosis, rheumatic disorders, allergic states, edematous states and other immune diseases.

Compared with the prior art, the invention has the following advantages: (1) the content and chromatographic purity of ACTH (human sequence) in the crude peptide are greatly improved through Fmoc solid-phase synthesis with stepwise synthesis method. (2) The Fmoc solid-phase synthesis method with stepwise condensation technology can simplify the post-treatment process, greatly simplify the reaction procedure, and reduce the loss of products in the post-treatment stage. The required intermediates or products are anchored on the solid carrier, and the excess unreacted reactant and reagents can be directly removed by filtration and washing. The operation is simple, easy to realize automation, and is conducive to industrial scale-up. Moreover, the peptide of about 40 amino acid sequence length can be easily synthesized. While, in the liquid phase synthesis method, the mixture of unreacted reactant, reagents and target intermediates or products need to be separated and purified by crystallization or even column chromatography, Liquid phase synthesis requires more operational steps, longer production cycles, and is usually used for peptide synthesis of the amino acid sequence length within 10. (3) The conventional coupling process for C-15 position cannot make the reaction completely, resulting in the deletion peptide impurities, reducing the yield of the target product, increasing the content of impurities and the difficulty of subsequent purification. Through the screening of various coupling method and the optimization of the process conditions, the reaction in this step is complete, the deletion peptide impurities are reduced, the yield of product is improved, and the difficulty of purification is reduced. (4) The method of reversed-phase high-pressure purification has the advantages of strong separation capacity, good purification effect, less impurities and simple operation. The purity of ACTH (human sequence) or analogue thereof prepared in the invention is more than 99%, the product has a good stability, and the preparation yield is ≥63%.

DESCRIPTION OF THE EMBODIMENTS

Figure 1:
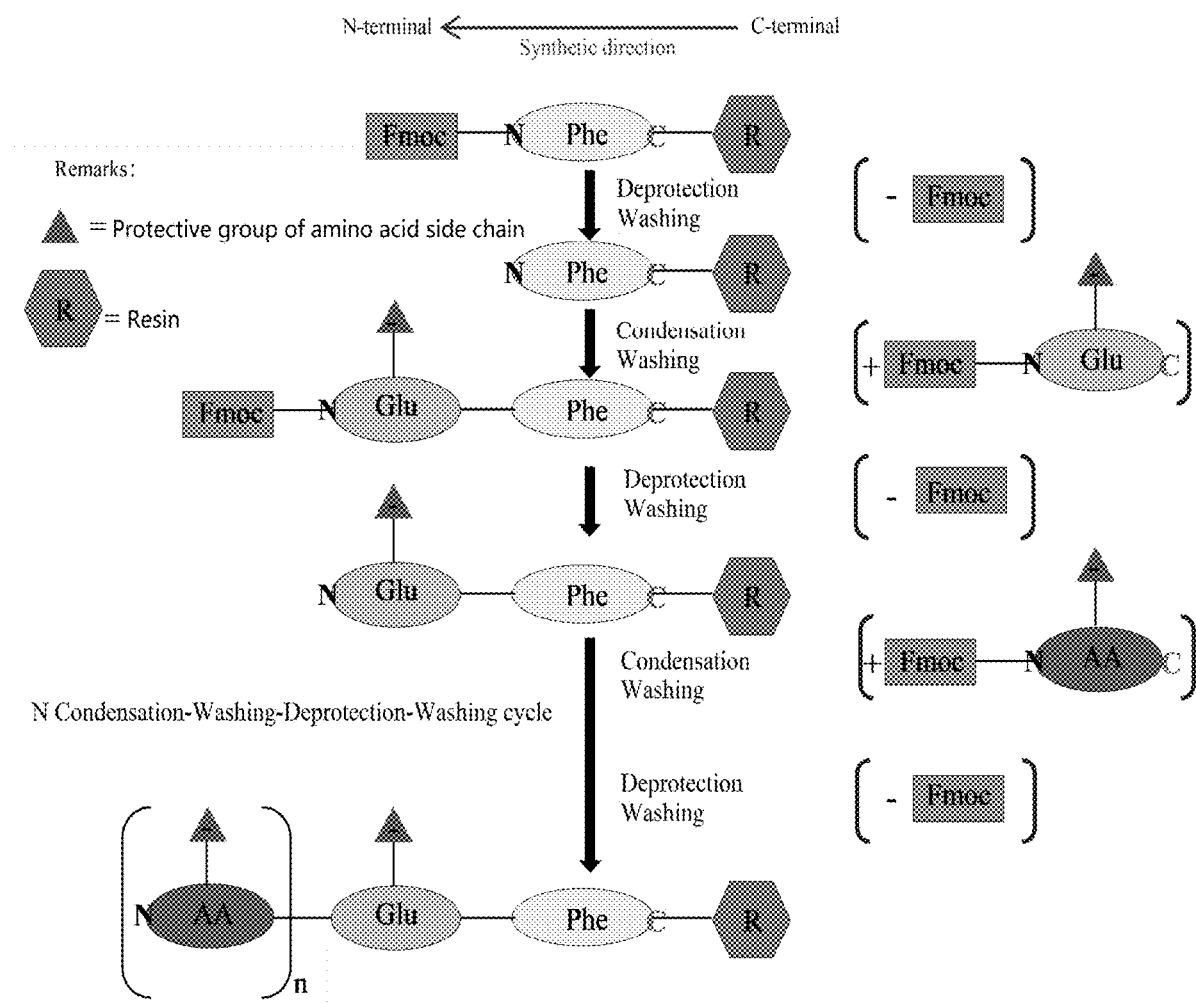
FIG. 1 is a flow chart of the stepwise condensation of solid-phase synthesis method of the present invention.

In order to facilitate those skilled in the art to understand the content of the present invention, the technical solutions of the invention will be further described below in conjunction with the examples, but the following contents should not limit the scope of the invention claimed by the appended claims in any way.
The materials and reagents used in the following examples can be obtained from commercial channels without special instructions. Amino acids are L-type amino acids without special instructions Example 1. Preparation of Fmoc-Phe-Resin 500 g of 2-triphenylmethylchloromethane resin was added to 5 L DCM and was swelled for 1 h, 4.25 mol DIPEA and 0.75 mol Fmoc-Phe-OH were added to react at room temperature for 4 h to obtain Fmoc-Phe-resin. 1.25 L DIPEA/methanol (volume ratio 1:9) solution was added to react for 0.5 h to cap the unreacted sites. The Fmoc-Phe-resin was filtrated and washed one time with 5 L DCM, then the resin was dried and washed three times with methanol, the amount of methanol used for each washing was 5 L. The Fmoc-Phe-resin was dried under vacuum to constant weight at room temperature, and the substitution was determined to be 0.7 mmol/g.

Example 2. Preparation of Fmoc-Glu(OtBu)-Phe-Resin

1) Resin swelling: 500 g of Fmoc-Phe-resin with substitution of 0.7 mmol/g prepared in example 1, namely, the molar amount of Fmoc-Phe was 0.35 mol, was added into the reactor, and 5 L DMF solution containing 50 g HOBt was added to fully swell Fmoc-Phe-resin.
2) Deprotection reaction: 5 L of deprotection reagent was added (20% piperidine/DMF solution, by volume ratio) to step 1), the mixture was stirred and reacted for 20 min, the resin was dried, and the deprotection reaction was repeated for 3 times until the deprotection reaction was complete. After the deprotection reaction, 5 L DMF solution once time was used to wash for 8 times in total to obtain Fmoc-Phe-resin.
3) Activation: 1.75 mol of Fmoc-Glu(OtBu)-OH was added into 5 L DMF solution, then 1.75 mol of Oxyma Pure and 1.75 mol of DIC were added respectively, and the mixture was reacted for 30 mins at room temperature to obtain the activated solution of Fmoc-Glu(OtBu)-OH;
4) Condensation reaction: the activated solution of Fmoc-Glu(OtBu)-OH was added to the Phe-resin obtained in step 2) to react for 3 h at 30° C., the resin was filtered and washed with DMF for 8 times to obtain Fmoc-Glu(OtBu)-Phe-resin. The reaction was monitored by the method of Ninhydrin Test. If the test result was negative, the next reaction was conducted. If the test result was positive, the above steps 3) to 4) condensation reaction was repeated until the test result was negative.

Example 3. Preparation of Fmoc-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe-Resin Refer to the method described in step 2)-4) of example 2, that was, each coupling amino acid was subjected to deprotection reaction, activation reaction and condensation reaction to the Fmoc-Glu(OtBu)-Phe-resin prepared in example 2. The amino acids were coupled according to the amino acid sequence of ACTH (human sequence) from the C-terminal to the N-terminal in the order of 3-14, the sequence of coupling amino acids was as follows: Fmoc-Leu-OH, Fmoc-Pro-OH, Fmoc-Phe-OH, Fmoc-Ala-OH, Fmoc-Glu(OtBu)-OH, Fmoc-Ala-OH, Fmoc-Ser(tBu)-OH, Fmoc-Glu(OtBu)-OH, Fmoc-Asp(OtBu)-OH, Fmoc-Glu(OtBu)-OH, Fmoc-Ala-OH, Fmoc-Gly-OH.

Example 4a. Preparation of Fmoc-Asn(Trt)-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe-Resin 1) 50 g of Fmoc-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe-resin prepared in example 3 was taken, 500 mL of deprotection reagent (20% piperidine/DMF solution, by volume ratio) was added to the resin. The mixture was stirred and reacted for 20 min, the resin was dried, and the deprotection reaction was repeated for 3 times until the deprotection reaction was complete. After the deprotection reaction, 500 mL DMF solution each time was used to wash for 8 times in total. The reaction product Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe-resin was evenly divided into 21 parts and respectively added into independent peptide reactor.

2) Preparation of Fmoc-Asn(Trt)-OH activated solution: several activated solutions were respectively prepared, 4.2 mmol Fmoc-Asn(Trt)-OH was added to 25 mL DMF solution for each solution, and then 4.2 mmol condensation reagent as shown in Table 1 was added to react at room temperature for 30 mins.

3) Each activated solution of Fmoc-Asn(Trt)-OH was added into the polypeptide reactor respectively for condensation reaction. The reaction temperature, type of condensation reagent and reaction time were shown in Table 1, wherein the amount of urea or sodium perchlorate was 0.1 Kg. After the reaction, the resin was filtered and washed with DMF for 8 times. During the reaction, the method of Ninhydrin Test was used to directly qualitatively detect whether the reaction was completed or not. Fmoc-Asn(Trt)-Gly-Ala-Glu(OtBu)-Asp(OtBu)-Glu(OtBu)-Ser(tBu)-Ala-Glu(OtBu)-Ala-Ph e-Pro-Leu-Glu(OtBu)-Phe-resin was cut with 85% trifluoroacetic acid solution, the resulting solution was precipitated with ether, and the precipitate was dissolved with water. The chromatographic purity of 15 peptide, the residue of substrate 14 peptide and the racemic impurity of D-Asn-15 peptide were determined by HPLC, the details were shown in Table 1:

TABLE 1

Condensation reactions under different reaction conditions

Figure 2:
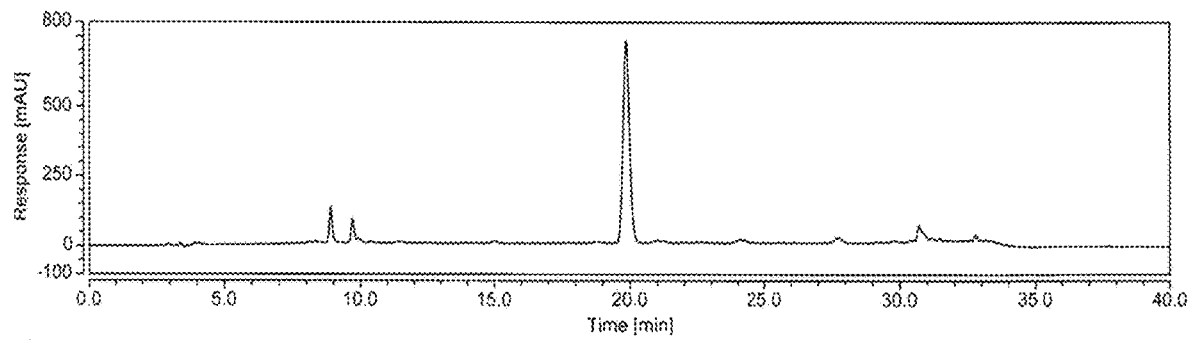
FIG. 2 is a liquid chromatogram of condensation of peptide 15 in example 4 at 20° C. for 20 h, using DIC/Oxyma Pure/urea as condensation agent.
Figure 3:
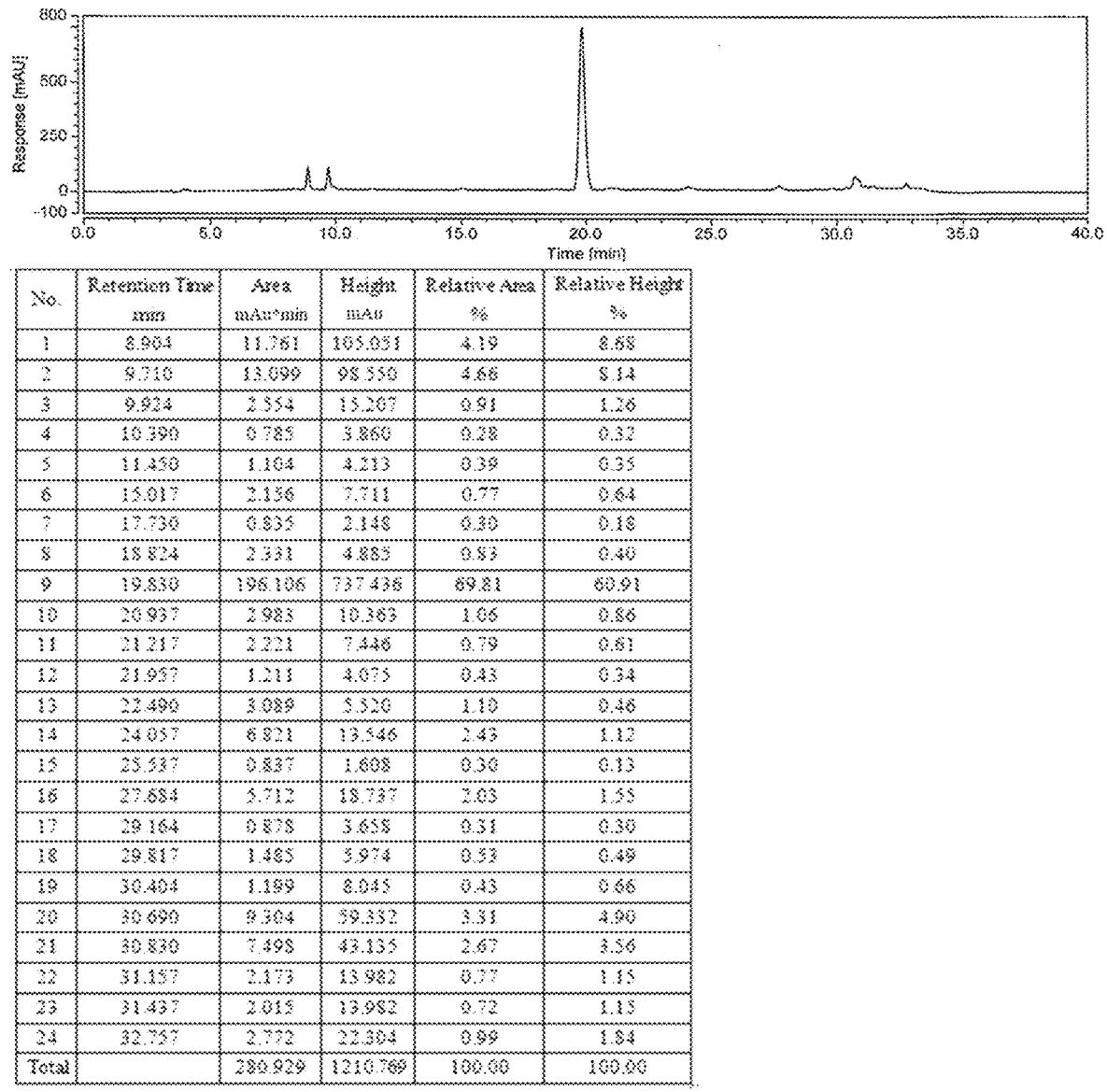
FIG. 3 is a liquid chromatogram of condensation of peptide 15 in example 4 at 30° C. for 20 h, using DIC/HOBt/NaClO$_4$ as condensation agent.
Figure 4:
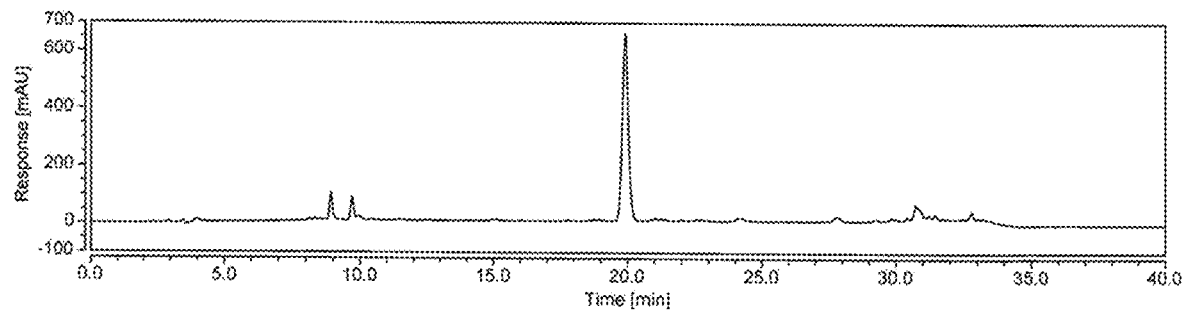
FIG. 4 is a liquid chromatogram of condensation of peptide 15 in example 4 at 35° C. for 20 h, using TBTU/DIPEA/HOBt as condensation agent.
Figure 5:
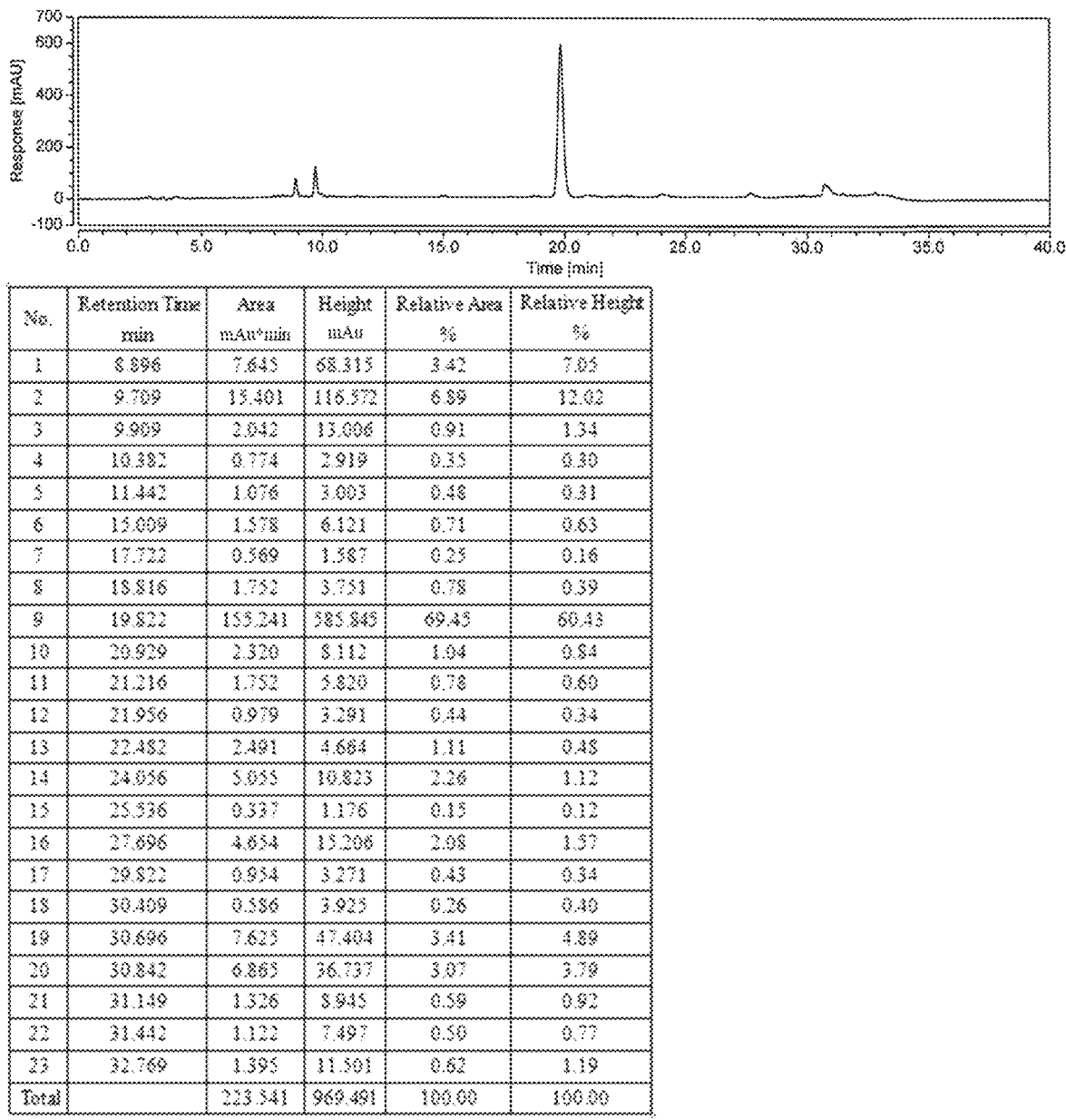
FIG. 5 is a liquid chromatogram of condensation of peptide 15 in example 4 at 40° C. for 3 h, using DIC/Oxyma Pure as condensation agent.
Figure 6:
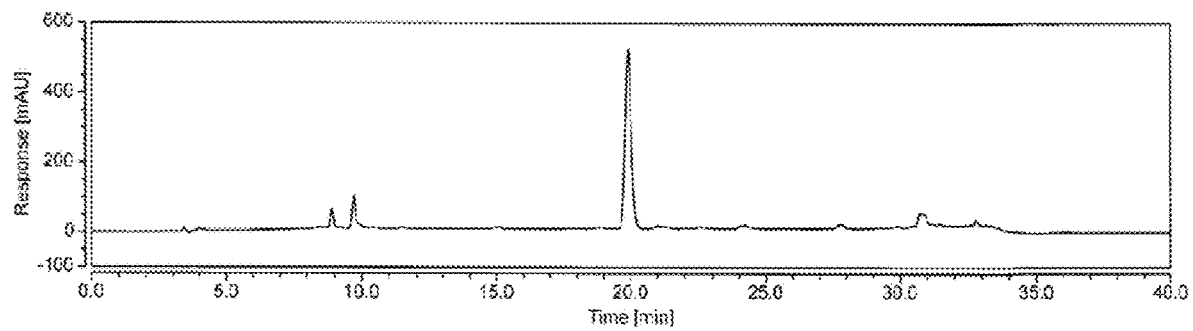
FIG. 6 is a liquid chromatogram of condensation of peptide 15 in example 4 at 45° C. for 3 h, using DIC/HOBt as condensation agent.
Figure 7:
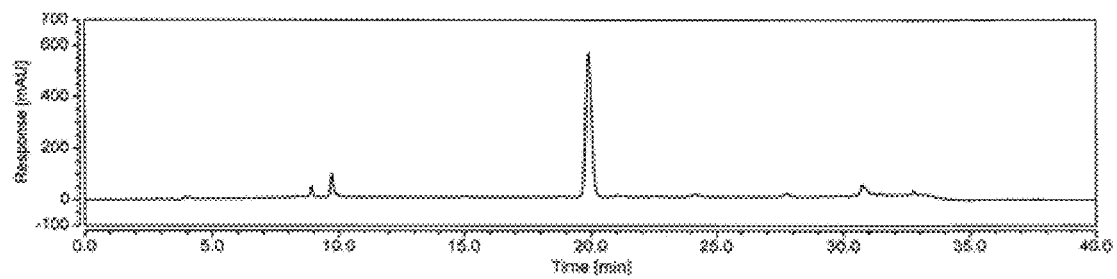
FIG. 7 is a liquid chromatogram of condensation of peptide 15 in example 4 at 50° C. for 3 h, using DIC/HOBt as condensation agent.
Figure 8:
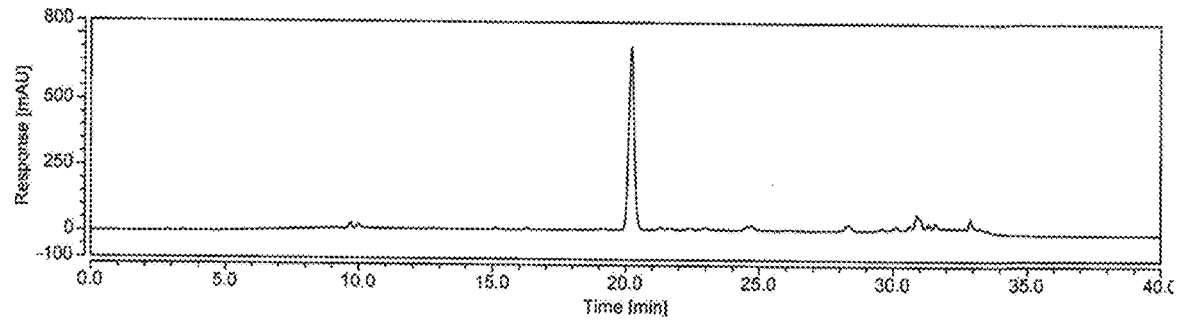
FIG. 8 is a liquid chromatogram of condensation of peptide 15 in example 4 at 50° C. for 3 h, using DIC/HOBt/urea as condensation agent.
Figure 9:
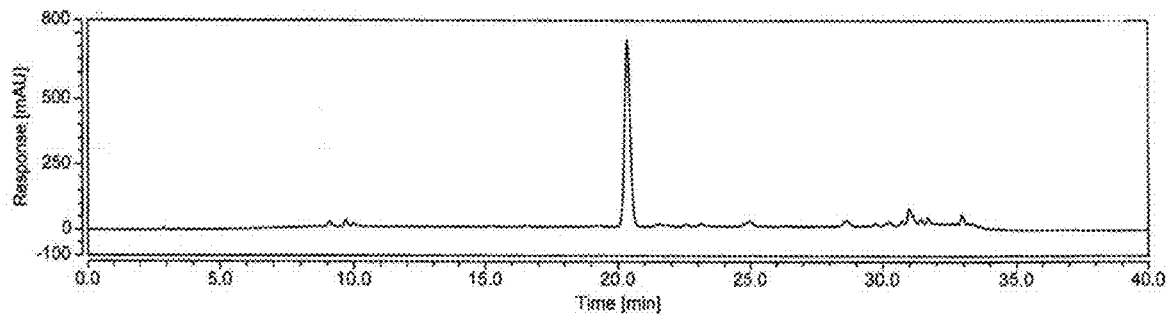
FIG. 9 is a liquid chromatogram of condensation of peptide 15 in example 4 at 50° C. for 3 h, using DIC/HOBt/NaClO$_4$ as condensation agent.
Figure 10:
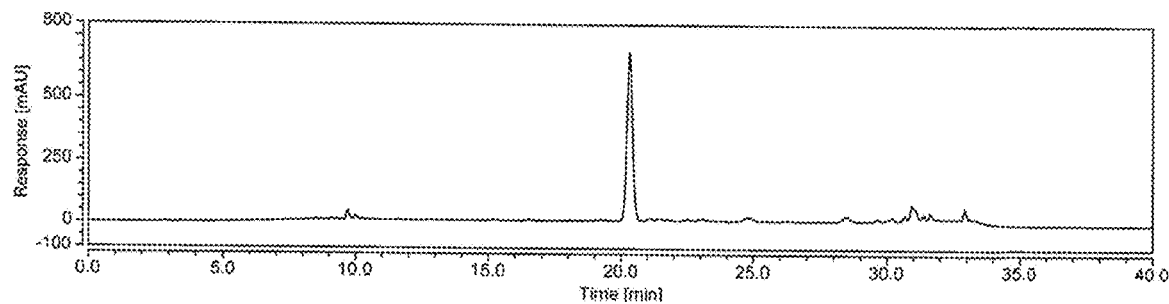
FIG. 10 is a liquid chromatogram of condensation of peptide 15 in example 4 at 60° C. for 3 h, using DIC/HOBt as condensation agent.

| # | Temperature of reaction | Type of condensation reagent | Time of reaction/h | Detection of ninhydrin | Chromatographic purity of 15 peptides | Residue of substrate 14 peptide | Racemic impurity of D-Asn-15 peptide | Appended drawings |
|---|---|---|---|---|---|---|---|---|
| 1. | 20° C. | DIC/Oxyma Pure | 3 | positive | — | — | — | — |
| 2. | | DIC/Oxyma Pure | 8 | positive | — | — | — | — |
| 3. | | DIC/Oxyma Pure | 20 | positive | — | — | — | — |
| 4. | | DIC/Oxyma Pure/urea | 3 | positive | — | — | — | — |
| 5. | | DIC/Oxyma Pure/urea | 8 | positive | — | — | — | — |
| 6. | | DIC/Oxyma Pure/urea | 20 | positive | 69.51% | 5.19% | not detected | FIG. 2 |
| 7. | 30° C. | DIC/HOBt | 3 | positive | — | — | — | — |
| 8. | | DIC/HOBt | 8 | positive | — | — | — | — |
| 9. | | DIC/HOBt | 20 | positive | — | — | — | — |
| 10. | | DIC/HOBt/NaClO$_4$ | 3 | positive | — | — | — | — |
| 11. | | DIC/HOBt/NaClO$_4$ | 8 | positive | — | — | — | — |
| 12. | | DIC/HOBt/NaClO$_4$ | 20 | positive | 69.81% | 4.19% | not detected | FIG. 3 |
| 13. | 35° C. | TBTU/DIPEA/HOBt | 3 | positive | — | — | — | — |
| 14. | | TBTU/DIPEA/HOBt | 8 | positive | — | — | — | — |
| 15. | | TBTU/DIPEA/HOBt | 20 | positive | 68.75% | 4.16% | not detected | FIG. 4 |
| 16. | 40° C. | DIC/Oxyma Pure | 3 | — | 69.45% | 3.42% | not detected | FIG. 5 |
| 17. | 45° C. | DIC/HOBt | 3 | — | 69.80% | 3.03% | not detected | FIG. 6 |
| 18. | 50° C. | DIC/HOBt | 3 | — | 71.06% | 2.28% | not detected | FIG. 7 |
| 19. | | DIC/HOBt/urea | 3 | — | 68.00% | 0.20% | not detected | FIG. 8 |
| 20. | | DIC/HOBt/NaClO$_4$ | 3 | — | 69.16% | 1.03% | not detected | FIG 9 |
| 21. | 60° C. | DIC/HOBt | 3 | — | 65.75% | 0.30% | 1.11% | FIG. 10 |

In the above table, the 15 peptide was H-Asn-Gly-Ala-Glu-Asp-Glu-Ser-Ala-Glu-Ala-Phe-Pro-Leu-Glu-Phe-OH; The 14 peptide was H-Gly-Ala-Glu-Asp-Glu-Ser-Ala-Glu-Ala-Phe-Pro-Leu-Glu-Phe-OH; The racemic impurity of D-Asn-15 peptide was H-(D-Asn)-Gly-Ala-Glu-Asp-Glu-Ser-Ala-Glu-Ala-Phe-Pro-Leu-Glu-Phe-OH.

The results showed that the residue of 14 substrate peptide was always more than 4% by using a variety of condensation reagents, repeating condensation times and prolonging condensation time when the reaction temperature was controlled at 20-35° C., which indicating that the reaction was not complete. When the reaction temperature was 40-60° C., the residue of 14 substrate peptide was controlled to be less than 4%. Especially when the reaction temperature was 50° C., the condensation rate could be significantly improved by adding appropriate amount of urea or NaClO$_4$ to DIC/HOBt condensation reagent. Because the urea added was more helpful to the improvement of condensation rate, and the residue of 14 substrate peptide was better controlled at 0.20%.

Example 4b 950 g of Fmoc-Gly-Ala-Glu(OtBu)-Asp(OtBu)-Glu(OtBu)-Ser(tBu)-Ala-Glu(OtBu)-Ala-Phe-Pro-Leu-Glu(OtBu)-Phe-resin prepared in example 3 was condensed under the optimal condition (#19) in Table 1, that was, the condensation reaction was conducted with Fmoc-Asn(Trt)-OH in the presence of the condensation reagent of DIC/HOBt/urea, and the obtained intermediate was used as the upstream raw material of example 5.

Example 5. Preparation of Fmoc-Ser(tBu)-Tyr(tBu)-Ser(tBu)-Met-Glu(OtBu)-His(Trt)-Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala- Glu(OtBu)-Asp(OtBu)-Glu(OtBu)-Ser(tBu)-Ala-Glu(OtBu)-Ala-Phe-Pro-Leu-Glu(OtBu)-Phe-Resin Refer to the method described in steps 2)-4) of example 2, each coupling amino acid was subjected to deprotection reaction, activation reaction and condensation reaction in the polypeptide reactor of example 4b. The amino acids were coupled according to the amino acid sequence of ACTH (human sequence) from the C-terminal to the N-terminal in the order of 16-39, the sequence of coupling amino acids were as follows: Fmoc-Pro-OH, Fmoc-Tyr(tBu)-OH, Fmoc-Val-OH, Fmoc-Lys(Boc)-OH, Fmoc-Val-OH, Fmoc-Pro-OH, Fmoc-Arg(Pbf)-OH, Fmoc-Arg(Pbf)-OH, Fmoc-Lys(Boc)-OH, Fmoc-Lys(Boc)-OH, Fmoc-Gly-OH, Fmoc-Val-OH, Fmoc-Pro-OH, Fmoc-Lys(Boc)-OH, Fmoc-Gly-OH, Fmoc-Trp(Boc)-OH, Fmoc-Arg(Pbf)-OH, Fmoc-Phe-OH, Fmoc-His(Trt)-OH, Fmoc-Glu(OtBu)-OH, Fmoc-Met-OH, Fmoc-Ser(tBu)-OH, Fmoc-Tyr(tBu)-OH, Fmoc-Ser(tBu)-OH. At the end of the coupling, the peptidyl-resin of ACTH (human sequence) with protective groups was obtained.

Example 6. Preparation of H-Ser(tBu)-Tyr(tBu)-Ser(tBu)-Met-Glu(OtBu)-His(Trt)-Phe-Arg(Pbf)-Trp(Boc)-Gly-Lys(Boc)-Pro-Val-Gly-Lys(Boc)-Lys(Boc)-Arg(Pbf)-Arg(Pbf)-Pro-Val-Lys(Boc)-Val-Tyr(tBu)-Pro-Asn(Trt)-Gly-Ala- Glu(OtBu)-Asp(OtBu)-Glu(OtBu)-Ser(tBu)-Ala-Glu(OtBu)-Ala-Phe-Pro-Leu-Glu(OtBu)-Phe-Resin 5 L of deprotection reagent (20% piperidine/DMF solution) was added and stirred, the reaction was conducted for 20 min, the resin was dried, the deprotection reaction was repeated for 3 times until the deprotection reaction was complete. After deprotection reaction, the resin was washed 8 times with 5 L DMF solution each time. Then, 5 L methanol solution was added to wash for 8 times, and the resin was filtered and dried under vacuum at 40° C. to obtain 1.75 Kg of the peptidyl-resin of ACTH (human sequence) without the N-terminal protection by Fmoc.

Figure 11:
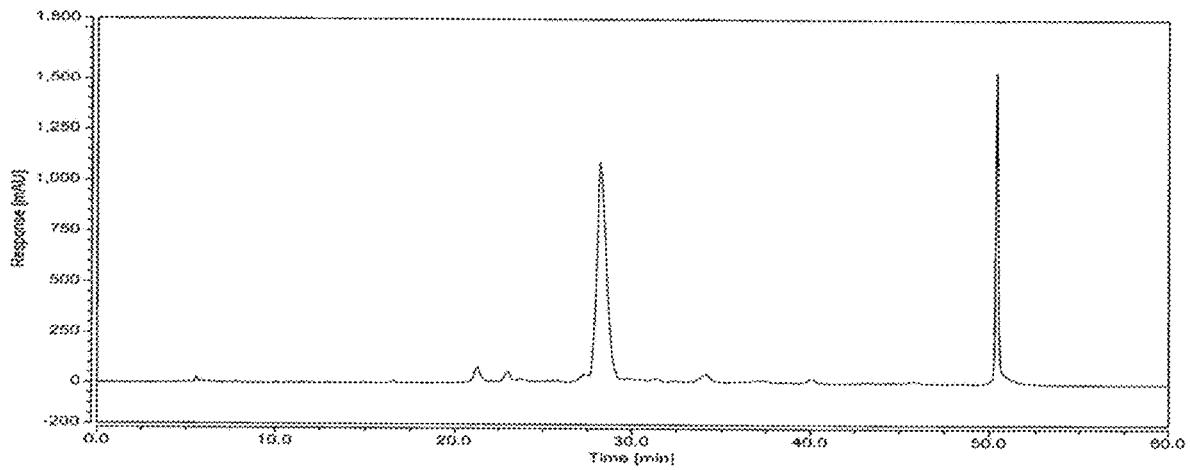
FIG. 11 is a liquid chromatogram of the crude peptide of ACTH (human sequence) in Example 7.

Example 7. Preparation of Crude Peptide of ACTH (Human Sequence) H-Ser-Tyr-Ser-Met-Glu-His-Phe-Arg-Trp-Gly-Lys-Pro-Val-Gly-Lys-Lys-Arg-Arg-Pro-Val-Lys-Val-Tyr-Pro-Asn-Gly-Ala-Glu-Asp-Glu-Ser-Ala-Glu-Ala-Phe-Pro-Leu-Glu-Phe-OH 1.75 Kg peptidyl-resin prepared in example 6 was added to 17.5 L cleavage cocktail which was precooled to −12° C. to react for 2 h (the cleavage cocktail was composed of 90% volume of trifluoroacetic acid and 10% volume of scavengers, in which the scavengers was composed of 1% phenol, 1% anisole, 1% dimethyl sulfide, 1% 1,2-ethanedithiol, 1% triethylsilane, 1% triisopropylsilane and 4% water in volume concentration), the temperature of the whole reaction was controlled not more than 40° C. After the reaction, the product was filtered and the filtrate was collected. The part of the cleavage cocktail was removed by reducing the pressure and concentrating the filtrate, and then the filtrate was slowly added to 17.5 L methyl tert-butyl ether which was precooled to −12° C. for precipitation. The wet solid was collected by centrifugation and washed with 87.5 L methyl tert-butyl ether. The solid was collected, dissolved with water and freeze-dried. 0.75 Kg solid crude peptide was obtained with purity of 68.96% and content of the target peptide of 48% (i.e. 0.36 Kg target peptide). As shown in FIG. 11, the peak time of the target peptide was 28.176 mins.

Example 8. Purification of Crude Peptide of ACTH (Human Sequence) H-Ser-Tyr-Ser-Met-Glu-His-Phe-Arg-Trp-Gly-Lys-Pro-Val-Gly-Lys-Lys-Arg-Arg-Pro-Val-Lys-Val-Tyr-Pro-Asn-Gly-Ala-Glu-Asp-Glu-Ser-Ala-Glu-Ala-Phe-Pro-Leu-Glu-Phe-OH 1. Treatment of sample: 0.75 Kg of crude peptide of ACTH (human sequence) obtained in example 7 was taken to dissolve in 37.5 L acetonitrile water solution with the volume ratio of acetonitrile:water=30:70, the crude peptide was stirred to dissolve completely and filtered with 0.45 μm filter membrane, and then the filtrate was collected for use.

2. The first purification:
Conditions of purification:
Chromatographic column: DAC-20 dynamic axial compression column with octadecylsilane chemically bonded silica as stationary phase;
Column diameter and packing length: 20*25 cm;
Mobile phase A: Tris aqueous solution with molar concentration of 0.1 mol/L, pH was adjusted to 8.0 by ammonia water;
Mobile phase B: acetonitrile;
Flow rate: 80 mL/min;
The detection wavelength: 280 nm.
Gradient: B %: 30-60% (50 mins), the injection volume was 20 g.
Process of purification: the chromatographic column was equilibrated with mobile phase A and then loaded with 5 L sample solution. Linear gradient elution was conducted for 50 mins and the target peptide solution with purity of more than 90% was collected. The yield of target peptide was 79%.

3. The second purification:
Conditions of purification:
Chromatographic column: DAC-20 dynamic axial compression column with octadecylsilane chemically bonded silica as stationary phase;
Column diameter and packing length: 20*25 cm;
Mobile phase A: Ammonium sulfate aqueous solution with molar concentration of 0.1 mol/L, pH was adjusted to 3.0 by sulfuric acid;
Mobile phase B: acetonitrile;
Flow rate: 80 mL/min;
The detection wavelength: 280 nm.
Gradient: B %: 30-60% (50 mins), the injection volume was 20 g.
Process of purification: the chromatographic column was equilibrated with mobile phase A and then loaded with 1 L sample solution. Linear gradient elution was conducted for 50 mins and the target peptide solution with purity of more than 99% was collected. The yield of target peptide was 86%.

4. Desalting and ion control:
Conditions of desalting:
Chromatographic column: DAC-20 dynamic axial compression column with octadecylsilane chemically bonded silica as stationary phase;
Column diameter and packing length: 20*25 cm;
Mobile phase A: Acetic acid aqueous solution with concentration of 0.1%;
Mobile phase B: acetonitrile;
Flow rate: 80 mL/min;
The detection wavelength: 280 nm.
Gradient: B %: 30-60% (50 mins), the injection volume was 20 g.
Process of desalting: the chromatographic column was equilibrated with mobile phase A and then loaded with 1 L sample solution. Linear gradient elution for was conducted 50 mins and the target peptide solution was collected. The yield of target peptide was 95%.

Figure 12:
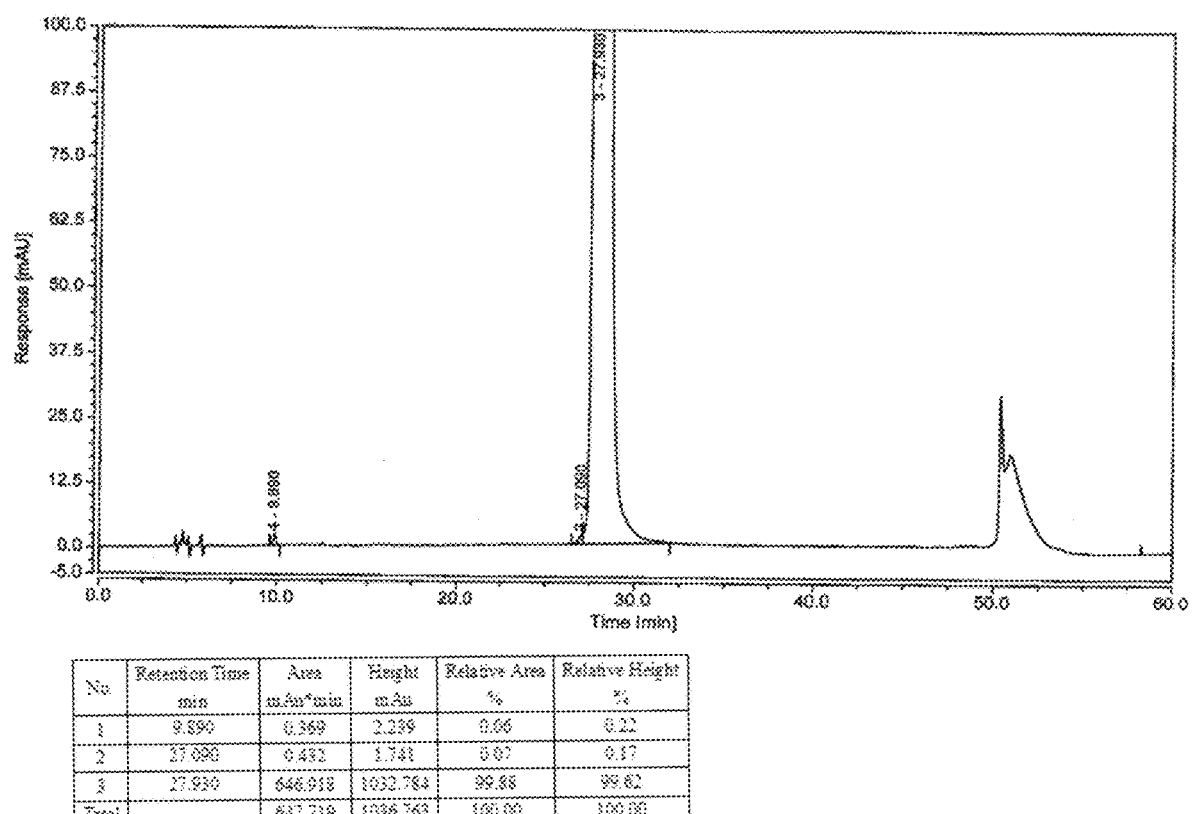
FIG. 12 is a liquid chromatogram of the pure ACTH (human sequence) in example 8.

5. Freeze drying
The target peptide solution obtained in the previous step was transferred to a stainless steel tray with appropriate size, and then detected by HPLC after freeze drying. The purity of ACTH acetate (human sequence, SEQ ID NO: 3) was 99.88% (as shown in FIG. 12, the peak time of main peak was 27.930 min, the content of maximum single impurity was 0.07%, and the content of total impurities was 0.13%). The target peptide collected was 258 g, the content was 90%, and the molar yield was 65%. The accurate molecular weight detected by high-resolution mass spectrometry was 4538.232 Da, which was consistent with the theoretical accurate molecular weight of ACTH (human sequence).

Example 9

Figure 13:
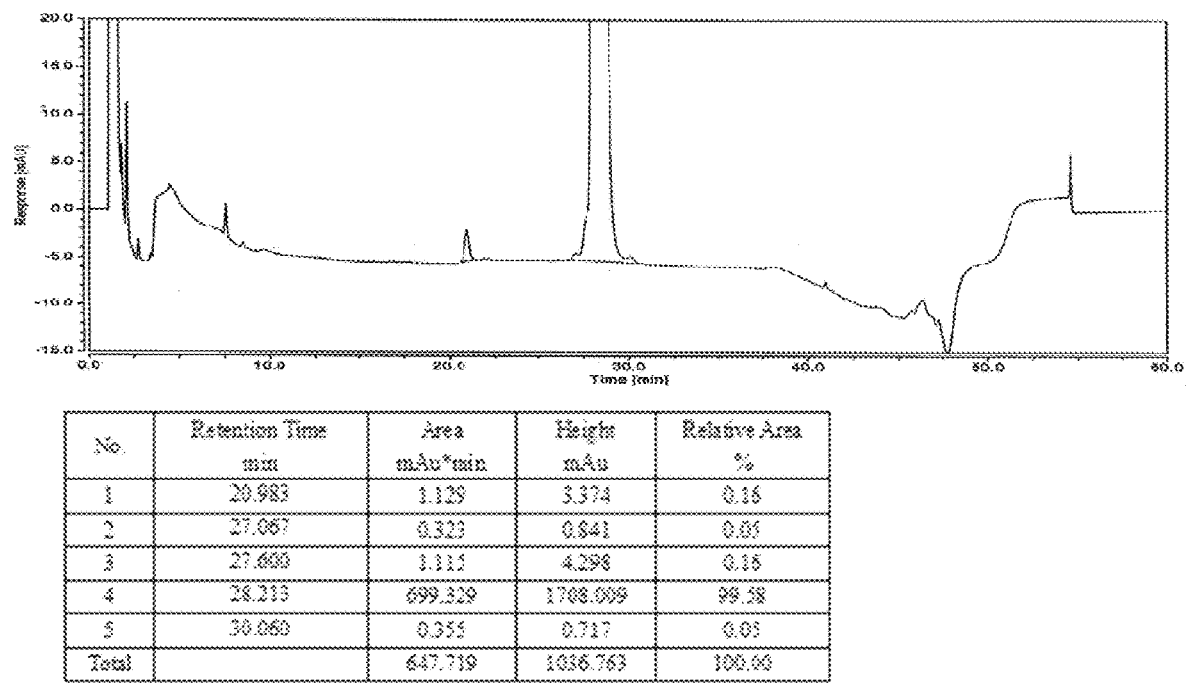
FIG. 13 is a liquid chromatogram of the pure ACTH (human sequence) analogue in example 9.

Referring to the method of example 4b-8, the amino acid of Asp(Trt) at position 15 was replaced with Asn(Trt) to obtain the ACTH (human sequence) analogue (SEQ ID NO: 4, H-Ser-Tyr-Ser-Met-Glu-His-Phe-Arg-Trp-Gly-Lys-Pro-Val-Gly-Lys-Lys-Arg-Arg-Pro-Val-Lys-Val-Tyr-Pro-Asp-Gly-Ala-Glu-Asp-Glu-Ser-Ala-Glu-Ala-Phe-Pro-Leu-Glu-Phe-OH) with the purity of 99.58% (as shown in FIG. 13, the peak time of the main peak was 28.213 min, the content of maximum single impurity was 0.16%, and the content of total impurities was 0.42%). The target peptide collected was 255 g, the content was 89%, and the molar yield of the target peptide was 63%. The accurate molecular weight detected by high-resolution mass spectrometry was 4537.232 Da, which was consistent with the theoretical accurate molecular weight of ACTH (human sequence) analogue.

Example 10 (Comparative Example)

Figure 14:
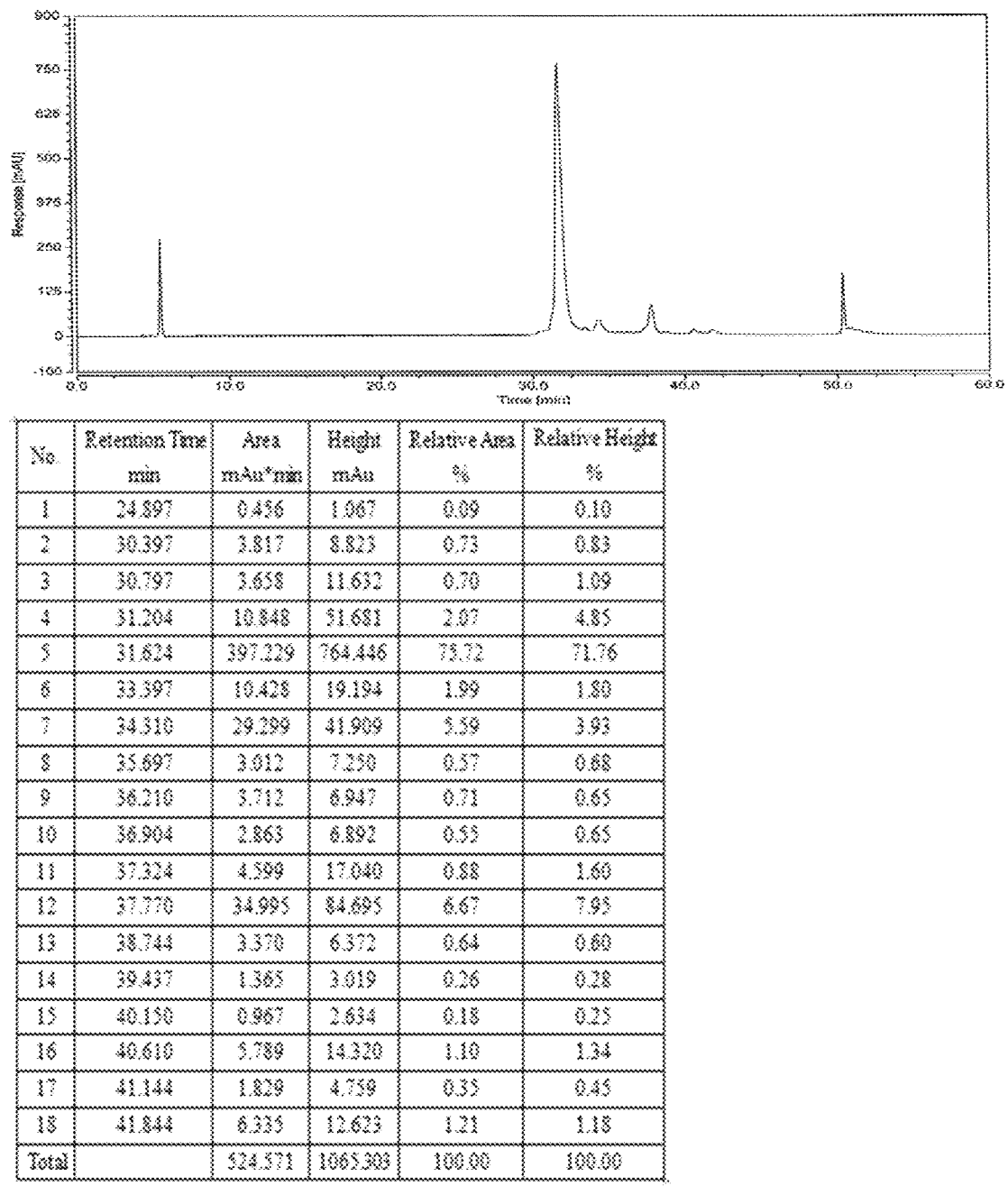
FIG. 14 is a liquid chromatogram of ACTH (human sequence) obtained by the method of U.S. Pat. No. 3,953,415 A in comparative example.

ACTH (human sequence) (SEQ ID NO: 3) was prepared strictly according to the specific steps from step 1 to step 14 in example 4 of U.S. Pat. No. 3,953,415. The total yield was 17%, and the purity of ACTH (human sequence) was only 75.72%, as shown in FIG. 14.

Example 11 Study of Stability

The samples prepared in example 8 were packed in double-layer medical low-density polyethylene bags and a layer of aluminum-plastic composite bags and stored at 2-8° C. for evaluation at 1, 2, 3 and 6 months respectively. The stability results of the samples after acceleration for 6 months were shown in Table 2:

TABLE 2

Stability results of acceleration for 6 months

| Accelerated test | | | | | | | |
|---|---|---|---|---|---|---|---|
| Inspection items | Detection method | Start | 1 month | 2 months | 3 months | 6 months | Conclusion |
| | | | | Result | | | |
| Character | Visual | White powder | White powder | White powder | White powder | White powder | Qualified |
| Related substances (maximum single impurity) | HPLC | 0.07% | 0.17% | 0.17% | 0.16% | 0.11% | Qualified |
| Related substances (total impurities) | HPLC | 0.13% | 0.29% | 0.29% | 0.38% | 0.39% | |
| The purity of chromatographic | HPLC | 99.88% | 99.71% | 99.71% | 99.62% | 99.61% | Qualified |
| Moisture | Karl Fischer | 5.0% | 7.3% | 7.5% | 8.4% | 8.3% | Qualified |
| Polymer | HPLC | 0.03% | 0.05% | 0.03% | 0.06% | 0.04% | Qualified |

The results showed that the character, related substances, purity of chromatographic, moisture and polymer of ACTH (human sequence SEQ ID NO: 3) had no obvious change trend at 2-8° C. It was suggested that the ACTH (human sequence SEQ ID NO: 3) was stable under this storage condition. The polymer refers to an impurity with a molecular weight greater than that of ACTH (human sequence SEQ ID NO: 3).

The samples prepared in example 9 were packed in double-layer medical low-density polyethylene bags and a layer of aluminum-plastic composite bags and stored at 2-8° C. for evaluation at 1, 2, 3 and 6 months respectively. The stability results of the samples after acceleration for 6 months were shown in Table 3:

TABLE 3

Stability results of acceleration for 6 months

Accelerated test

| Inspection items | Detection method | Start | 1 month | 2 months Result | 3 months | 6 months | Conclusion |
|---|---|---|---|---|---|---|---|
| Character | Visual | White powder | White powder | White powder | White powder | White powder | Qualified |
| Related substances (maximum single impurity) | HPLC | 0.16% | 0.24% | 0.17% | 0.27% | 0.10% | Qualified |
| Related substances (total impurities) | HPLC | 0.42% | 0.42% | 0.43% | 0.46% | 0.49% | |
| The purity of chromatographic | HPLC | 99.58% | 99.58% | 99.57% | 99.54% | 99.51% | Qualified |
| Moisture | Karl Fischer | 5.2% | 7.5% | 7.6% | 8.5% | 8.6% | Qualified |
| Polymer | HPLC | 0.03% | 0.04% | 0.05% | 0.06% | 0.06% | Qualified |

The results showed that the character, related substances, purity of chromatographic, moisture and polymer of ACTH analogue (human sequence SEQ ID NO: 4) had no obvious change trend at 2-8° C. It was suggested that the ACTH analogue (human sequence SEQ ID NO: 4) was stable under this storage condition. The polymer refers to an impurity with a molecular weight greater than that of ACTH analogue (human sequence SEQ ID NO: 4).

Example 12 Data of Security (1) Study of Activity In Vitro

ACTH was a receptor agonist of melanocortin receptor 2 (MC2R). The combination of ACTH and MC2R could stimulate the signal pathway of the downstream and change the signal factors such as calcium ions and cAMP. The binding ability of ACTH and MC2R was determined by detecting calcium ion signals, and then the cell activity of ACTH in vitro was judged.

The samples in example 8 and example 10 were taken for activity study in vitro. CHO-K1 cells expressing MC2R were cultured in 10 cm vessels and stored at 37° C. and 5% $CO_2$.

The results showed that high-purity ACTH (human sequence SEQ ID NO: 3, 99.88%) and low-purity ACTH (human sequence SEQ ID NO: 3, 75.72%) had binding ability to melanocortin receptor 2 (MC2R) and showed biological activity. The half inhibitory concentration ($EC_{50}$) of high-purity ACTH was 180.2 nM, the half inhibitory concentration of low-purity ACTH was 287.9 nM. The lower the half inhibitory concentration, the higher the activity. Therefore, the activity of high-purity ACTH was better than that of low-purity ACTH, and the activity of the former was 1.6 times that of the latter. The specific activity test datas were shown in Table 4:

TABLE 4

Activity test datas

| The source of sample | Bottom | Top | HillSlope | $EC_{50}$ (nM) |
|---|---|---|---|---|
| Example 8 | −2.739 | 100.9 | 0.9745 | 180.2 |
| Example 10 | −1.846 | 94.88 | 1.249 | 287.9 |

(2) Study of Toxicity In Vitro

The cardiac metabolic toxicity of drugs was judged by detecting the affinity between drugs and heart receptor protein (hERG) in vitro. The higher the affinity between the drug and the hERG receptor, the lower the half inhibitory concentration, which indicated that the lower the dose required for its toxicity to the heart, and the stronger the metabolic toxicity to the heart.

The samples in example 8, example 10 and positive control drug of dofetilide were taken for toxicity study in vitro. The results showed that the $IC_{50}$ of high-purity ACTH and low-purity ACTH were more than 10000 nM, and the $IC_{50}$ of positive control drug was 2.09 nM. Therefore, the toxic dose of high-purity ACTH and low-purity ACTH was much higher than that of the positive control drug, showing no cardiac metabolic toxicity. The specific metabolic toxicity datas were shown in Table 5:

TABLE 5

Datas of cardiac metabolic toxicity

| The source of sample | $IC_{50}$ (nM) | MaxDose (nM) | % Inh @ MaxDose |
|---|---|---|---|
| Exemple 8 | >10000 | 10000 | −1.28 |
| Exemple 10 | >10000 | 10000 | 12.47 |
| positive control drug | 2.090 | 10000 | 104.47 |

What is claimed is:

1. A composition containing adrenocorticotropic hormone or analogue thereof and impurity, wherein the purity of the adrenocorticotropic hormone or analogue thereof is ≥99%, the content of the maximum single impurity is ≤0.5%, and the content of the total impurities is ≤1%, and wherein the sequence of the adrenocorticotropic hormone from the N-terminal to the C-terminal is (SEQ ID NO: 4)
SYSMEHFRWGKPVGKKRRPVKVYPDGAEDESAEAFPLEF.

2. The composition according to claim 1, wherein the purity of the adrenocorticotropic hormone or analogue thereof is ≥99.5%, and the content of the total impurity is ≤0.5%.

3. A pharmaceutical composition comprising the composition of claim 1, and a medicinal carrier.

4. A method for preparing the composition according to claim 1, the method comprising coupling amino acids from C-terminal to N-terminal according to the amino acid sequence shown in SEQ ID NO: 4 by Fmoc solid-phase synthesis, thereby creating a synthesis product, and purifying the synthesis product to obtain the composition containing adrenocorticotropic hormone or adrenocorticotropic hormone analogue.

5. The method for preparing the composition according to claim 4, further comprising:
1) coupling amino acids from C- to N-terminal according to the amino acid sequence shown in SEQ ID NO: 4 by Fmoc solid-phase synthesis to obtain a peptidyl-resin of adrenocorticotropic hormone or analogue thereof with protective groups;
2) contacting the peptidyl-resin of adrenocorticotropic hormone or analogue thereof with protective groups with a cleavage cocktail thereby cleaving the peptide chain of adrenocorticotropic hormone or analogue thereof from the resin, and thereby removing the protective groups of the peptide chain, in order to obtain a solution containing adrenocorticotropic hormone or analogue thereof;
3) treating the solution containing adrenocorticotropic hormone or analogue thereof with a precipitation reagent to obtain a crude product of the adrenocorticotropic hormone or analogue thereof; and
4) purifying the crude product of the adrenocorticotropic hormone or analogue thereof by liquid chromatography to obtain the composition containing the adrenocorticotropic hormone or analogue thereof.

6. The method for preparing the composition according to claim 5, wherein in step 1), the amino acids are coupled stepwise or as fragments, with N-terminal protection by Fmoc group.

7. The method for preparing the composition according to claim 5, wherein in step 1), the resin used in the solid-phase synthesis method is Wang resin, 2-triphenylmethylchloromethane resin, Rink Amide AM Resin, Rink Amide MBHA Resin, Rink Amide Resin or resin connected with Fmoc-Phe-OH.

8. The method for preparing the composition according to claim 5, wherein step 1) comprises:
i). swelling an Fmoc-$AA_n$-resin by a first organic solvent, wherein $AA_n$ represents a polypeptide with n amino acid residues have been connected to the resin, wherein n is a natural number from 1 to 38; and wherein the structure of each amino acid in the polypeptide is the same or different, with the N-terminal amino acid being protected by Fmoc, Boc or Cbz group, and the side-chain of each amino acid having or without protective group;
ii). deprotecting the Fmoc-$AA_n$-resin with a second organic solvent until the Fmoc protecting group is removed, to obtain a deprotected H-$AA_n$-resin by washing with a third organic solvent;
iii). reacting Fmoc-$AA_m$-OH with an activation reagent in the first organic solvent to obtain an activated Fmoc-$AA_m$-OH derivative solution, wherein $AA_m$ is the (n+1)th amino acid from the C-terminus of SEQ ID NO: 4; wherein step iii) may be completed either before or after step i) or step ii);
iv). mixing the activated Fmoc-$AA_m$-OH derivative solution with the deprotected H-$AA_n$-resin to obtain an Fmoc-$AA_{(n+1)}$-resin through a coupling reaction, and washing the Fmoc-$AA_{(n+1)}$-resin with the third organic solvent; and,
v). repeating step ii) to step iv) to connect the remaining amino acid residues of SEQ ID NO: 4 to the Fmoc-$AA_{(n+1)}$-resin to obtain the adrenocorticotropic hormone or analogue thereof peptidyl-resin with side-chain protective groups.

9. The method for preparing the composition according to claim 8, wherein the first organic solvent in step i) and step iii) is an aprotic solvent.

10. The method for preparing the composition according to claim 8, wherein the second organic solvent in step ii) is an aprotic solvent containing an organic base.

11. The method for preparing the composition according to claim 8, wherein the third organic solvent in step ii) is the first organic solvent or alcohol solvent.

12. The method for preparing the composition according to claim 8, wherein the activation reagent in step iii) is one of composition of DIC, HBTU and Oxyma Pure, composition of DIC and Oxyma Pure, composition of DIC and HOBt, composition of DIEA, TBTU and HOBt, composition of DIEA and PyBop.

13. The method for preparing the composition according to claim 8, wherein in step iv), the reaction temperature for coupling is 10-35° C. and the reaction time is 0.5-5 h besides the coupling at C-15 position; and the reaction temperature for coupling amino acid at C-15 position in step iv) is 40-60° C. and the reaction time is 0.5-16 h.

14. The method for preparing the composition according to claim 13, wherein urea or perchlorate is added to the reaction mixture in step iv) when coupling the amino acid at C-15 position.

15. The method for preparing the composition according to claim 14, wherein the mass ratio of urea or perchlorate to Fmoc-Phe-resin is 0.1:1-1:1.

16. The method for preparing the composition according to claim 5, wherein the peptidyl-resin of adrenocorticotropic hormone or analogue thereof with protective groups obtained in step 1) is deprotected with the second organic solvent, washed with the third organic solvent, and washed with the fourth organic solvent, wherein the fourth organic solvent comprises one or more of methanol, ethanol and DCM.

17. The method for preparing the composition according to claim 5, wherein the cleavage cocktail comprises trifluoroacetic acid and scavengers in step 2), and the scavengers is composed of one or more of phenol, benzyl sulfide, dimethyl sulfide, 1,2-ethanedithiol, triethylsilane, triisopropylsilane or water; the volume ratio of the scavengers and trifluoroacetic acid is 1:4-1:19.

18. The method for preparing the composition according to claim 5, wherein the precipitation reagent in step 3) is an ether solvent.

19. The method according to claim 7, wherein the resin is 2-triphenylmethylchloromethane resin.

* * * * *

SEQUENCE LISTING

<160> NUMBER OF SEQ ID NOS: 29

<210> SEQ ID NO 1
<211> LENGTH: 39
<212> TYPE: PRT
<213> ORGANISM: Sus scrofa
<220> FEATURE:
<223> OTHER INFORMATION: Porcine adrenocorticotropic hormone

<400> SEQUENCE: 1

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Leu Ala
            20                  25                  30

Glu Ala Phe Pro Leu Glu Phe
        35

<210> SEQ ID NO 2
<211> LENGTH: 39
<212> TYPE: PRT
<213> ORGANISM: Sus scrofa
<220> FEATURE:
<223> OTHER INFORMATION: Porcine N-25 deamidated adrenocorticotropic
      hormone

<400> SEQUENCE: 2

Ser Tyr Ser Met Glu His Phe Arg Trp Gly Lys Pro Val Gly Lys Lys
1               5                   10                  15

Arg Arg Pro Val Lys Val Tyr Pro Asp Gly Ala Glu Asp Glu Leu Ala
            20                  25                  30

Glu Ala Phe Pro Leu Glu Phe
        35

<210> SEQ ID NO 3
<211> LENGTH: 39
<212> TYPE: PRT
<213> ORGANISM: Homo sapiens
<220> FEATURE:
<223> OTHER INFORMATION: adrenocorticotropic hormone  (human sequence)

<400> SEQUENCE: 3

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu Phe
        35

<210> SEQ ID NO 4
<211> LENGTH: 39
<212> TYPE: PRT
<213> ORGANISM: Artificial Sequence
<220> FEATURE:
<223> OTHER INFORMATION: N-25 deamidated human ACTH or analogue

<400> SEQUENCE: 4

Ser Tyr Ser Met Glu His Phe Arg Trp Gly Lys Pro Val Gly Lys Lys
1               5                   10                  15

Arg Arg Pro Val Lys Val Tyr Pro Asp Gly Ala Glu Asp Glu Ser Ala
            20                  25                  30

Glu Ala Phe Pro Leu Glu Phe
        35

```
<210> SEQ ID NO 5
<211> LENGTH: 15
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (1)..(1)
<223> OTHER INFORMATION: Asparagine is protected by Trt.
<220> FEATURE:
<221> NAME/KEY: MOD_RES
<222> LOCATION: (4)..(4)
<223> OTHER INFORMATION: Glutamic acid is protected by OtBu.
<220> FEATURE:
<221> NAME/KEY: MOD_RES
<222> LOCATION: (5)..(5)
<223> OTHER INFORMATION: Aspartic acid is protected by OtBu.
<220> FEATURE:
<221> NAME/KEY: MOD_RES
<222> LOCATION: (6)..(6)
<223> OTHER INFORMATION: Glutamic acid is protected by OtBu.
<220> FEATURE:
<221> NAME/KEY: MOD_RES
<222> LOCATION: (7)..(7)
<223> OTHER INFORMATION: Serine is protected by tBu.
<220> FEATURE:
<221> NAME/KEY: MOD_RES
<222> LOCATION: (9)..(9)
<223> OTHER INFORMATION: Glutamic acid is protected by OtBu.
<220> FEATURE:
<221> NAME/KEY: MOD_RES
<222> LOCATION: (14)..(14)
<223> OTHER INFORMATION: Glutamic acid is protected by OtBu.

<400> SEQUENCE: 5

Asn Gly Ala Glu Asp Glu Ser Ala Glu Ala Phe Pro Leu Glu Phe
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (2)..(2)
<223> OTHER INFORMATION: Asparagine is protected by Trt.
<220> FEATURE:
<221> NAME/KEY: MOD_RES
<222> LOCATION: (5)..(5)
<223> OTHER INFORMATION: Glutamic acid is protected by OtBu.
<220> FEATURE:
<221> NAME/KEY: MOD_RES
<222> LOCATION: (6)..(6)
<223> OTHER INFORMATION: Aspartic acid is protected by OtBu.
<220> FEATURE:
<221> NAME/KEY: MOD_RES
<222> LOCATION: (7)..(7)
<223> OTHER INFORMATION: Glutamic acid is protected by OtBu.
<220> FEATURE:
<221> NAME/KEY: MOD_RES
<222> LOCATION: (8)..(8)
<223> OTHER INFORMATION: Serine is protected by tBu.
<220> FEATURE:
<221> NAME/KEY: MOD_RES
<222> LOCATION: (10)..(10)
<223> OTHER INFORMATION: Glutamic acid is protected by OtBu.
<220> FEATURE:
<221> NAME/KEY: MOD_RES
<222> LOCATION: (15)..(15)
<223> OTHER INFORMATION: Glutamic acid is protected by OtBu.
<220> FEATURE:
<223> OTHER INFORMATION: The sequence is synthesized
```

```
<400> SEQUENCE: 6

Pro Asn Gly Ala Glu Asp Glu Ser Ala Glu Ala Phe Pro Leu Glu Phe
1               5                   10                  15

<210> SEQ ID NO 7
<211> LENGTH: 17
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (1)..(1)
<223> OTHER INFORMATION: Tyrosine is protected by tBu.
<220> FEATURE:
<221> NAME/KEY: MOD_RES
<222> LOCATION: (3)..(3)
<223> OTHER INFORMATION: Asparagine is protected by Trt.
<220> FEATURE:
<221> NAME/KEY: MOD_RES
<222> LOCATION: (6)..(6)
<223> OTHER INFORMATION: Glutamic acid is protected by OtBu.
<220> FEATURE:
<221> NAME/KEY: MOD_RES
<222> LOCATION: (7)..(7)
<223> OTHER INFORMATION: Aspartic acid is protected by OtBu.
<220> FEATURE:
<221> NAME/KEY: MOD_RES
<222> LOCATION: (8)..(8)
<223> OTHER INFORMATION: Glutamic acid is protected by OtBu.
<220> FEATURE:
<221> NAME/KEY: MOD_RES
<222> LOCATION: (9)..(9)
<223> OTHER INFORMATION: Serine is protected by tBu.
<220> FEATURE:
<221> NAME/KEY: MOD_RES
<222> LOCATION: (11)..(11)
<223> OTHER INFORMATION: Glutamic acid is protected by OtBu.
<220> FEATURE:
<221> NAME/KEY: MOD_RES
<222> LOCATION: (16)..(16)
<223> OTHER INFORMATION: Glutamic acid is protected by OtBu.

<400> SEQUENCE: 7

Tyr Pro Asn Gly Ala Glu Asp Glu Ser Ala Glu Ala Phe Pro Leu Glu
1               5                   10                  15

Phe

<210> SEQ ID NO 8
<211> LENGTH: 18
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (2)..(2)
<223> OTHER INFORMATION: Tyrosine is protected by tBu.
<220> FEATURE:
<221> NAME/KEY: MOD_RES
<222> LOCATION: (4)..(4)
<223> OTHER INFORMATION: Asparagine is protected by Trt.
<220> FEATURE:
<221> NAME/KEY: MOD_RES
<222> LOCATION: (7)..(7)
<223> OTHER INFORMATION: Glutamic acid is protected by OtBu.
<220> FEATURE:
<221> NAME/KEY: MOD_RES
<222> LOCATION: (8)..(8)
<223> OTHER INFORMATION: Aspartic acid is protected by OtBu.
<220> FEATURE:
<221> NAME/KEY: MOD_RES
<222> LOCATION: (9)..(9)
<223> OTHER INFORMATION: Glutamic acid is protected by OtBu.
```

```
<220> FEATURE:
<221> NAME/KEY: MOD_RES
<222> LOCATION: (10)..(10)
<223> OTHER INFORMATION: Serine is protected by tBu.
<220> FEATURE:
<221> NAME/KEY: MOD_RES
<222> LOCATION: (12)..(12)
<223> OTHER INFORMATION: Glutamic acid is protected by OtBu.
<220> FEATURE:
<221> NAME/KEY: MOD_RES
<222> LOCATION: (17)..(17)
<223> OTHER INFORMATION: Glutamic acid is protected by OtBu.

<400> SEQUENCE: 8

Val Tyr Pro Asn Gly Ala Glu Asp Glu Ser Ala Glu Ala Phe Pro Leu
1               5                   10                  15

Glu Phe

<210> SEQ ID NO 9
<211> LENGTH: 19
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (1)..(1)
<223> OTHER INFORMATION: Lysine is protected by Boc.
<220> FEATURE:
<221> NAME/KEY: MOD_RES
<222> LOCATION: (3)..(3)
<223> OTHER INFORMATION: Tyrosine is protected by tBu.
<220> FEATURE:
<221> NAME/KEY: MOD_RES
<222> LOCATION: (5)..(5)
<223> OTHER INFORMATION: Asparagine is protected by Trt.
<220> FEATURE:
<221> NAME/KEY: MOD_RES
<222> LOCATION: (8)..(8)
<223> OTHER INFORMATION: Glutamic acid is protected by OtBu.
<220> FEATURE:
<221> NAME/KEY: MOD_RES
<222> LOCATION: (9)..(9)
<223> OTHER INFORMATION: Aspartic acid is protected by OtBu.
<220> FEATURE:
<221> NAME/KEY: MOD_RES
<222> LOCATION: (10)..(10)
<223> OTHER INFORMATION: Glutamic acid is protected by OtBu.
<220> FEATURE:
<221> NAME/KEY: MOD_RES
<222> LOCATION: (11)..(11)
<223> OTHER INFORMATION: Serine is protected by tBu.
<220> FEATURE:
<221> NAME/KEY: MOD_RES
<222> LOCATION: (13)..(13)
<223> OTHER INFORMATION: Glutamic acid is protected by OtBu.
<220> FEATURE:
<221> NAME/KEY: MOD_RES
<222> LOCATION: (18)..(18)
<223> OTHER INFORMATION: Glutamic acid is protected by OtBu.

<400> SEQUENCE: 9

Lys Val Tyr Pro Asn Gly Ala Glu Asp Glu Ser Ala Glu Ala Phe Pro
1               5                   10                  15

Leu Glu Phe

<210> SEQ ID NO 10
<211> LENGTH: 20
<212> TYPE: PRT
<213> ORGANISM: Artificial Sequence
<220> FEATURE:
<223> OTHER INFORMATION: The sequence is synthesized
<220> FEATURE:
```

```
<221> NAME/KEY: MOD_RES
<222> LOCATION: (2)..(2)
<223> OTHER INFORMATION: Lysine is protected by Boc.
<220> FEATURE:
<221> NAME/KEY: MOD_RES
<222> LOCATION: (4)..(4)
<223> OTHER INFORMATION: Tyrosine is protected by tBu.
<220> FEATURE:
<221> NAME/KEY: MOD_RES
<222> LOCATION: (6)..(6)
<223> OTHER INFORMATION: Asparagine is protected by Trt.
<220> FEATURE:
<221> NAME/KEY: MOD_RES
<222> LOCATION: (9)..(9)
<223> OTHER INFORMATION: Glutamic acid is protected by OtBu.
<220> FEATURE:
<221> NAME/KEY: MOD_RES
<222> LOCATION: (10)..(10)
<223> OTHER INFORMATION: Aspartic acid is protected by OtBu.
<220> FEATURE:
<221> NAME/KEY: MOD_RES
<222> LOCATION: (11)..(11)
<223> OTHER INFORMATION: Glutamic acid is protected by OtBu.
<220> FEATURE:
<221> NAME/KEY: MOD_RES
<222> LOCATION: (12)..(12)
<223> OTHER INFORMATION: Serine is protected by tBu.
<220> FEATURE:
<221> NAME/KEY: MOD_RES
<222> LOCATION: (14)..(14)
<223> OTHER INFORMATION: Glutamic acid is protected by OtBu.
<220> FEATURE:
<221> NAME/KEY: MOD_RES
<222> LOCATION: (19)..(19)
<223> OTHER INFORMATION: Glutamic acid is protected by OtBu.

<400> SEQUENCE: 10

Val Lys Val Tyr Pro Asn Gly Ala Glu Asp Glu Ser Ala Glu Ala Phe
1               5                   10                  15

Pro Leu Glu Phe
            20

<210> SEQ ID NO 11
<211> LENGTH: 21
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (3)..(3)
<223> OTHER INFORMATION: Lysine is protected by Boc.
<220> FEATURE:
<221> NAME/KEY: MOD_RES
<222> LOCATION: (5)..(5)
<223> OTHER INFORMATION: Tyrosine is protected by tBu.
<220> FEATURE:
<221> NAME/KEY: MOD_RES
<222> LOCATION: (7)..(7)
<223> OTHER INFORMATION: Asparagine is protected by Trt.
<220> FEATURE:
<221> NAME/KEY: MOD_RES
<222> LOCATION: (10)..(10)
<223> OTHER INFORMATION: Glutamic acid is protected by OtBu.
<220> FEATURE:
<221> NAME/KEY: MOD_RES
<222> LOCATION: (11)..(11)
<223> OTHER INFORMATION: Aspartic acid is protected by OtBu.
<220> FEATURE:
<221> NAME/KEY: MOD_RES
<222> LOCATION: (12)..(12)
<223> OTHER INFORMATION: Glutamic acid is protected by OtBu.
<220> FEATURE:
<221> NAME/KEY: MOD_RES
<222> LOCATION: (13)..(13)
<223> OTHER INFORMATION: Serine is protected by tBu.
```

```
<220> FEATURE:
<221> NAME/KEY: MOD_RES
<222> LOCATION: (15)..(15)
<223> OTHER INFORMATION: Glutamic acid is protected by OtBu.
<220> FEATURE:
<221> NAME/KEY: MOD_RES
<222> LOCATION: (20)..(20)
<223> OTHER INFORMATION: Glutamic acid is protected by OtBu.

<400> SEQUENCE: 11

Pro Val Lys Val Tyr Pro Asn Gly Ala Glu Asp Glu Ser Ala Glu Ala
1               5                   10                  15

Phe Pro Leu Glu Phe
            20

<210> SEQ ID NO 12
<211> LENGTH: 22
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (1)..(1)
<223> OTHER INFORMATION: Arginine is protected by Pbf.
<220> FEATURE:
<221> NAME/KEY: MOD_RES
<222> LOCATION: (4)..(4)
<223> OTHER INFORMATION: Lysine is protected by Boc.
<220> FEATURE:
<221> NAME/KEY: MOD_RES
<222> LOCATION: (6)..(6)
<223> OTHER INFORMATION: Tyrosine is protected by tBu.
<220> FEATURE:
<221> NAME/KEY: MOD_RES
<222> LOCATION: (8)..(8)
<223> OTHER INFORMATION: Asparagine is protected by Trt.
<220> FEATURE:
<221> NAME/KEY: MOD_RES
<222> LOCATION: (11)..(11)
<223> OTHER INFORMATION: Glutamic acid is protected by OtBu.
<220> FEATURE:
<221> NAME/KEY: MOD_RES
<222> LOCATION: (12)..(12)
<223> OTHER INFORMATION: Aspartic acid is protected by OtBu.
<220> FEATURE:
<221> NAME/KEY: MOD_RES
<222> LOCATION: (13)..(13)
<223> OTHER INFORMATION: Glutamic acid is protected by OtBu.
<220> FEATURE:
<221> NAME/KEY: MOD_RES
<222> LOCATION: (14)..(14)
<223> OTHER INFORMATION: Serine is protected by tBu.
<220> FEATURE:
<221> NAME/KEY: MOD_RES
<222> LOCATION: (16)..(16)
<223> OTHER INFORMATION: Glutamic acid is protected by OtBu.
<220> FEATURE:
<221> NAME/KEY: MOD_RES
<222> LOCATION: (21)..(21)
<223> OTHER INFORMATION: Glutamic acid is protected by OtBu.

<400> SEQUENCE: 12

Arg Pro Val Lys Val Tyr Pro Asn Gly Ala Glu Asp Glu Ser Ala Glu
1               5                   10                  15

Ala Phe Pro Leu Glu Phe
            20

<210> SEQ ID NO 13
<211> LENGTH: 23
<212> TYPE: PRT
<213> ORGANISM: Artificial Sequence
<220> FEATURE:
```

```
<223> OTHER INFORMATION: The sequence is synthesized
<220> FEATURE:
<221> NAME/KEY: MOD_RES
<222> LOCATION: (1)..(1)
<223> OTHER INFORMATION: Arginine is protected by Pbf.
<220> FEATURE:
<221> NAME/KEY: MOD_RES
<222> LOCATION: (2)..(2)
<223> OTHER INFORMATION: Arginine is protected by Pbf.
<220> FEATURE:
<221> NAME/KEY: MOD_RES
<222> LOCATION: (5)..(5)
<223> OTHER INFORMATION: Lysine is protected by Boc.
<220> FEATURE:
<221> NAME/KEY: MOD_RES
<222> LOCATION: (7)..(7)
<223> OTHER INFORMATION: Tyrosine is protected by tBu.
<220> FEATURE:
<221> NAME/KEY: MOD_RES
<222> LOCATION: (9)..(9)
<223> OTHER INFORMATION: Asparagine is protected by Trt.
<220> FEATURE:
<221> NAME/KEY: MOD_RES
<222> LOCATION: (12)..(12)
<223> OTHER INFORMATION: Glutamic acid is protected by OtBu.
<220> FEATURE:
<221> NAME/KEY: MOD_RES
<222> LOCATION: (13)..(13)
<223> OTHER INFORMATION: Aspartic acid is protected by OtBu.
<220> FEATURE:
<221> NAME/KEY: MOD_RES
<222> LOCATION: (14)..(14)
<223> OTHER INFORMATION: Glutamic acid is protected by OtBu.
<220> FEATURE:
<221> NAME/KEY: MOD_RES
<222> LOCATION: (15)..(15)
<223> OTHER INFORMATION: Serine is protected by tBu.
<220> FEATURE:
<221> NAME/KEY: MOD_RES
<222> LOCATION: (17)..(17)
<223> OTHER INFORMATION: Glutamic acid is protected by OtBu.
<220> FEATURE:
<221> NAME/KEY: MOD_RES
<222> LOCATION: (22)..(22)
<223> OTHER INFORMATION: Glutamic acid is protected by OtBu.

<400> SEQUENCE: 13

Arg Arg Pro Val Lys Val Tyr Pro Asn Gly Ala Glu Asp Glu Ser Ala
1               5                   10                  15

Glu Ala Phe Pro Leu Glu Phe
            20

<210> SEQ ID NO 14
<211> LENGTH: 24
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (1)..(1)
<223> OTHER INFORMATION: Lysine is protected by Boc.
<220> FEATURE:
<221> NAME/KEY: MOD_RES
<222> LOCATION: (2)..(2)
<223> OTHER INFORMATION: Arginine is protected by Pbf.
<220> FEATURE:
<221> NAME/KEY: MOD_RES
<222> LOCATION: (3)..(3)
<223> OTHER INFORMATION: Arginine is protected by Pbf.
<220> FEATURE:
<221> NAME/KEY: MOD_RES
<222> LOCATION: (6)..(6)
<223> OTHER INFORMATION: Lysine is protected by Boc.
<220> FEATURE:
<221> NAME/KEY: MOD_RES
```

```
<222> LOCATION: (8)..(8)
<223> OTHER INFORMATION: Tyrosine is protected by tBu.
<220> FEATURE:
<221> NAME/KEY: MOD_RES
<222> LOCATION: (10)..(10)
<223> OTHER INFORMATION: Asparagine is protected by Trt.
<220> FEATURE:
<221> NAME/KEY: MOD_RES
<222> LOCATION: (13)..(13)
<223> OTHER INFORMATION: Glutamic acid is protected by OtBu.
<220> FEATURE:
<221> NAME/KEY: MOD_RES
<222> LOCATION: (14)..(14)
<223> OTHER INFORMATION: Aspartic acid is protected by OtBu.
<220> FEATURE:
<221> NAME/KEY: MOD_RES
<222> LOCATION: (15)..(15)
<223> OTHER INFORMATION: Glutamic acid is protected by OtBu.
<220> FEATURE:
<221> NAME/KEY: MOD_RES
<222> LOCATION: (16)..(16)
<223> OTHER INFORMATION: Serine is protected by tBu.
<220> FEATURE:
<221> NAME/KEY: MOD_RES
<222> LOCATION: (18)..(18)
<223> OTHER INFORMATION: Glutamic acid is protected by OtBu.
<220> FEATURE:
<221> NAME/KEY: MOD_RES
<222> LOCATION: (23)..(23)
<223> OTHER INFORMATION: Glutamic acid is protected by OtBu.

<400> SEQUENCE: 14

Lys Arg Arg Pro Val Lys Val Tyr Pro Asn Gly Ala Glu Asp Glu Ser
1               5                   10                  15

Ala Glu Ala Phe Pro Leu Glu Phe
            20

<210> SEQ ID NO 15
<211> LENGTH: 25
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (1)..(1)
<223> OTHER INFORMATION: Lysine is protected by Boc.
<220> FEATURE:
<221> NAME/KEY: MOD_RES
<222> LOCATION: (2)..(2)
<223> OTHER INFORMATION: Lysine is protected by Boc.
<220> FEATURE:
<221> NAME/KEY: MOD_RES
<222> LOCATION: (3)..(3)
<223> OTHER INFORMATION: Arginine is protected by Pbf.
<220> FEATURE:
<221> NAME/KEY: MOD_RES
<222> LOCATION: (4)..(4)
<223> OTHER INFORMATION: Arginine is protected by Pbf.
<220> FEATURE:
<221> NAME/KEY: MOD_RES
<222> LOCATION: (7)..(7)
<223> OTHER INFORMATION: Lysine is protected by Boc.
<220> FEATURE:
<221> NAME/KEY: MOD_RES
<222> LOCATION: (9)..(9)
<223> OTHER INFORMATION: Tyrosine is protected by tBu.
<220> FEATURE:
<221> NAME/KEY: MOD_RES
<222> LOCATION: (11)..(11)
<223> OTHER INFORMATION: Asparagine is protected by Trt.
<220> FEATURE:
<221> NAME/KEY: MOD_RES
<222> LOCATION: (14)..(14)
<223> OTHER INFORMATION: Glutamic acid is protected by OtBu.
<220> FEATURE:
```

```
<221> NAME/KEY: MOD_RES
<222> LOCATION: (15)..(15)
<223> OTHER INFORMATION: Aspartic acid is protected by OtBu.
<220> FEATURE:
<221> NAME/KEY: MOD_RES
<222> LOCATION: (16)..(16)
<223> OTHER INFORMATION: Glutamic acid is protected by OtBu.
<220> FEATURE:
<221> NAME/KEY: MOD_RES
<222> LOCATION: (17)..(17)
<223> OTHER INFORMATION: Serine is protected by tBu.
<220> FEATURE:
<221> NAME/KEY: MOD_RES
<222> LOCATION: (19)..(19)
<223> OTHER INFORMATION: Glutamic acid is protected by OtBu.
<220> FEATURE:
<221> NAME/KEY: MOD_RES
<222> LOCATION: (24)..(24)
<223> OTHER INFORMATION: Glutamic acid is protected by OtBu.

<400> SEQUENCE: 15

Lys Lys Arg Arg Pro Val Lys Val Tyr Pro Asn Gly Ala Glu Asp Glu
1               5                   10                  15

Ser Ala Glu Ala Phe Pro Leu Glu Phe
            20                  25

<210> SEQ ID NO 16
<211> LENGTH: 26
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (2)..(2)
<223> OTHER INFORMATION: Lysine is protected by Boc.
<220> FEATURE:
<221> NAME/KEY: MOD_RES
<222> LOCATION: (3)..(3)
<223> OTHER INFORMATION: Lysine is protected by Boc.
<220> FEATURE:
<221> NAME/KEY: MOD_RES
<222> LOCATION: (4)..(4)
<223> OTHER INFORMATION: Arginine is protected by Pbf.
<220> FEATURE:
<221> NAME/KEY: MOD_RES
<222> LOCATION: (5)..(5)
<223> OTHER INFORMATION: Arginine is protected by Pbf.
<220> FEATURE:
<221> NAME/KEY: MOD_RES
<222> LOCATION: (8)..(8)
<223> OTHER INFORMATION: Lysine is protected by Boc.
<220> FEATURE:
<221> NAME/KEY: MOD_RES
<222> LOCATION: (10)..(10)
<223> OTHER INFORMATION: Tyrosine is protected by tBu.
<220> FEATURE:
<221> NAME/KEY: MOD_RES
<222> LOCATION: (12)..(12)
<223> OTHER INFORMATION: Asparagine is protected by Trt.
<220> FEATURE:
<221> NAME/KEY: MOD_RES
<222> LOCATION: (15)..(15)
<223> OTHER INFORMATION: Glutamic acid is protected by OtBu.
<220> FEATURE:
<221> NAME/KEY: MOD_RES
<222> LOCATION: (16)..(16)
<223> OTHER INFORMATION: Aspartic acid is protected by OtBu.
<220> FEATURE:
<221> NAME/KEY: MOD_RES
<222> LOCATION: (17)..(17)
<223> OTHER INFORMATION: Glutamic acid is protected by OtBu.
<220> FEATURE:
<221> NAME/KEY: MOD_RES
<222> LOCATION: (18)..(18)
<223> OTHER INFORMATION: Serine is protected by tBu.
```

-continued

```
<220> FEATURE:
<221> NAME/KEY: MOD_RES
<222> LOCATION: (20)..(20)
<223> OTHER INFORMATION: Glutamic acid is protected by OtBu.
<220> FEATURE:
<221> NAME/KEY: MOD_RES
<222> LOCATION: (25)..(25)
<223> OTHER INFORMATION: Glutamic acid is protected by OtBu.

<400> SEQUENCE: 16

Gly Lys Lys Arg Arg Pro Val Lys Val Tyr Pro Asn Gly Ala Glu Asp
1               5                   10                  15

Glu Ser Ala Glu Ala Phe Pro Leu Glu Phe
            20                  25

<210> SEQ ID NO 17
<211> LENGTH: 27
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (3)..(3)
<223> OTHER INFORMATION: Lysine is protected by Boc.
<220> FEATURE:
<221> NAME/KEY: MOD_RES
<222> LOCATION: (4)..(4)
<223> OTHER INFORMATION: Lysine is protected by Boc.
<220> FEATURE:
<221> NAME/KEY: MOD_RES
<222> LOCATION: (5)..(5)
<223> OTHER INFORMATION: Arginine is protected by Pbf.
<220> FEATURE:
<221> NAME/KEY: MOD_RES
<222> LOCATION: (6)..(6)
<223> OTHER INFORMATION: Arginine is protected by Pbf.
<220> FEATURE:
<221> NAME/KEY: MOD_RES
<222> LOCATION: (9)..(9)
<223> OTHER INFORMATION: Lysine is protected by Boc.
<220> FEATURE:
<221> NAME/KEY: MOD_RES
<222> LOCATION: (11)..(11)
<223> OTHER INFORMATION: Tyrosine is protected by tBu.
<220> FEATURE:
<221> NAME/KEY: MOD_RES
<222> LOCATION: (13)..(13)
<223> OTHER INFORMATION: Asparagine is protected by Trt.
<220> FEATURE:
<221> NAME/KEY: MOD_RES
<222> LOCATION: (16)..(16)
<223> OTHER INFORMATION: Glutamic acid is protected by OtBu.
<220> FEATURE:
<221> NAME/KEY: MOD_RES
<222> LOCATION: (17)..(17)
<223> OTHER INFORMATION: Aspartic acid is protected by OtBu.
<220> FEATURE:
<221> NAME/KEY: MOD_RES
<222> LOCATION: (18)..(18)
<223> OTHER INFORMATION: Glutamic acid is protected by OtBu.
<220> FEATURE:
<221> NAME/KEY: MOD_RES
<222> LOCATION: (19)..(19)
<223> OTHER INFORMATION: Serine is protected by tBu.
<220> FEATURE:
<221> NAME/KEY: MOD_RES
<222> LOCATION: (21)..(21)
<223> OTHER INFORMATION: Glutamic acid is protected by OtBu.
<220> FEATURE:
<221> NAME/KEY: MOD_RES
<222> LOCATION: (26)..(26)
<223> OTHER INFORMATION: Glutamic acid is protected by OtBu.

<400> SEQUENCE: 17
```

-continued

```
Val Gly Lys Lys Arg Arg Pro Val Lys Val Tyr Pro Asn Gly Ala Glu
1               5                   10                  15

Asp Glu Ser Ala Glu Ala Phe Pro Leu Glu Phe
            20                  25

<210> SEQ ID NO 18
<211> LENGTH: 28
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (4)..(4)
<223> OTHER INFORMATION: Lysine is protected by Boc.
<220> FEATURE:
<221> NAME/KEY: MOD_RES
<222> LOCATION: (5)..(5)
<223> OTHER INFORMATION: Lysine is protected by Boc.
<220> FEATURE:
<221> NAME/KEY: MOD_RES
<222> LOCATION: (6)..(6)
<223> OTHER INFORMATION: Arginine is protected by Pbf.
<220> FEATURE:
<221> NAME/KEY: MOD_RES
<222> LOCATION: (7)..(7)
<223> OTHER INFORMATION: Arginine is protected by Pbf.
<220> FEATURE:
<221> NAME/KEY: MOD_RES
<222> LOCATION: (10)..(10)
<223> OTHER INFORMATION: Lysine is protected by Boc.
<220> FEATURE:
<221> NAME/KEY: MOD_RES
<222> LOCATION: (12)..(12)
<223> OTHER INFORMATION: Tyrosine is protected by tBu.
<220> FEATURE:
<221> NAME/KEY: MOD_RES
<222> LOCATION: (14)..(14)
<223> OTHER INFORMATION: Asparagine is protected by Trt.
<220> FEATURE:
<221> NAME/KEY: MOD_RES
<222> LOCATION: (17)..(17)
<223> OTHER INFORMATION: Glutamic acid is protected by OtBu.
<220> FEATURE:
<221> NAME/KEY: MOD_RES
<222> LOCATION: (18)..(18)
<223> OTHER INFORMATION: Aspartic acid is protected by OtBu.
<220> FEATURE:
<221> NAME/KEY: MOD_RES
<222> LOCATION: (19)..(19)
<223> OTHER INFORMATION: Glutamic acid is protected by OtBu.
<220> FEATURE:
<221> NAME/KEY: MOD_RES
<222> LOCATION: (20)..(20)
<223> OTHER INFORMATION: Serine is protected by tBu.
<220> FEATURE:
<221> NAME/KEY: MOD_RES
<222> LOCATION: (22)..(22)
<223> OTHER INFORMATION: Glutamic acid is protected by OtBu.
<220> FEATURE:
<221> NAME/KEY: MOD_RES
<222> LOCATION: (27)..(27)
<223> OTHER INFORMATION: Glutamic acid is protected by OtBu.

<400> SEQUENCE: 18

Pro Val Gly Lys Lys Arg Arg Pro Val Lys Val Tyr Pro Asn Gly Ala
1               5                   10                  15

Glu Asp Glu Ser Ala Glu Ala Phe Pro Leu Glu Phe
            20                  25

<210> SEQ ID NO 19
<211> LENGTH: 29
<212> TYPE: PRT
<213> ORGANISM: Artificial Sequence
```

```
<220> FEATURE:
<223> OTHER INFORMATION: The sequence is synthesized
<220> FEATURE:
<221> NAME/KEY: MOD_RES
<222> LOCATION: (1)..(1)
<223> OTHER INFORMATION: Lysine is protected by Boc.
<220> FEATURE:
<221> NAME/KEY: MOD_RES
<222> LOCATION: (5)..(5)
<223> OTHER INFORMATION: Lysine is protected by Boc.
<220> FEATURE:
<221> NAME/KEY: MOD_RES
<222> LOCATION: (6)..(6)
<223> OTHER INFORMATION: Lysine is protected by Boc.
<220> FEATURE:
<221> NAME/KEY: MOD_RES
<222> LOCATION: (7)..(7)
<223> OTHER INFORMATION: Arginine is protected by Pbf.
<220> FEATURE:
<221> NAME/KEY: MOD_RES
<222> LOCATION: (8)..(8)
<223> OTHER INFORMATION: Arginine is protected by Pbf.
<220> FEATURE:
<221> NAME/KEY: MOD_RES
<222> LOCATION: (11)..(11)
<223> OTHER INFORMATION: Lysine is protected by Boc.
<220> FEATURE:
<221> NAME/KEY: MOD_RES
<222> LOCATION: (13)..(13)
<223> OTHER INFORMATION: Tyrosine is protected by tBu.
<220> FEATURE:
<221> NAME/KEY: MOD_RES
<222> LOCATION: (15)..(15)
<223> OTHER INFORMATION: Asparagine is protected by Trt.
<220> FEATURE:
<221> NAME/KEY: MOD_RES
<222> LOCATION: (18)..(18)
<223> OTHER INFORMATION: Glutamic acid is protected by OtBu.
<220> FEATURE:
<221> NAME/KEY: MOD_RES
<222> LOCATION: (19)..(19)
<223> OTHER INFORMATION: Aspartic acid is protected by OtBu.
<220> FEATURE:
<221> NAME/KEY: MOD_RES
<222> LOCATION: (20)..(20)
<223> OTHER INFORMATION: Glutamic acid is protected by OtBu.
<220> FEATURE:
<221> NAME/KEY: MOD_RES
<222> LOCATION: (21)..(21)
<223> OTHER INFORMATION: Serine is protected by tBu.
<220> FEATURE:
<221> NAME/KEY: MOD_RES
<222> LOCATION: (23)..(23)
<223> OTHER INFORMATION: Glutamic acid is protected by OtBu.
<220> FEATURE:
<221> NAME/KEY: MOD_RES
<222> LOCATION: (28)..(28)
<223> OTHER INFORMATION: Glutamic acid is protected by OtBu.

<400> SEQUENCE: 19

Lys Pro Val Gly Lys Lys Arg Arg Pro Val Lys Val Tyr Pro Asn Gly
1               5                   10                  15

Ala Glu Asp Glu Ser Ala Glu Ala Phe Pro Leu Glu Phe
            20                  25

<210> SEQ ID NO 20
<211> LENGTH: 30
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (2)..(2)
<223> OTHER INFORMATION: Lysine is protected by Boc.
<220> FEATURE:
```

```
<221> NAME/KEY: MOD_RES
<222> LOCATION: (6)..(6)
<223> OTHER INFORMATION: Lysine is protected by Boc.
<220> FEATURE:
<221> NAME/KEY: MOD_RES
<222> LOCATION: (7)..(7)
<223> OTHER INFORMATION: Lysine is protected by Boc.
<220> FEATURE:
<221> NAME/KEY: MOD_RES
<222> LOCATION: (8)..(8)
<223> OTHER INFORMATION: Arginine is protected by Pbf.
<220> FEATURE:
<221> NAME/KEY: MOD_RES
<222> LOCATION: (9)..(9)
<223> OTHER INFORMATION: Arginine is protected by Pbf.
<220> FEATURE:
<221> NAME/KEY: MOD_RES
<222> LOCATION: (12)..(12)
<223> OTHER INFORMATION: Lysine is protected by Boc.
<220> FEATURE:
<221> NAME/KEY: MOD_RES
<222> LOCATION: (14)..(14)
<223> OTHER INFORMATION: Tyrosine is protected by tBu.
<220> FEATURE:
<221> NAME/KEY: MOD_RES
<222> LOCATION: (16)..(16)
<223> OTHER INFORMATION: Asparagine is protected by Trt.
<220> FEATURE:
<221> NAME/KEY: MOD_RES
<222> LOCATION: (19)..(19)
<223> OTHER INFORMATION: Glutamic acid is protected by OtBu.
<220> FEATURE:
<221> NAME/KEY: MOD_RES
<222> LOCATION: (20)..(20)
<223> OTHER INFORMATION: Aspartic acid is protected by OtBu.
<220> FEATURE:
<221> NAME/KEY: MOD_RES
<222> LOCATION: (21)..(21)
<223> OTHER INFORMATION: Glutamic acid is protected by OtBu.
<220> FEATURE:
<221> NAME/KEY: MOD_RES
<222> LOCATION: (22)..(22)
<223> OTHER INFORMATION: Serine is protected by tBu.
<220> FEATURE:
<221> NAME/KEY: MOD_RES
<222> LOCATION: (24)..(24)
<223> OTHER INFORMATION: Glutamic acid is protected by OtBu.
<220> FEATURE:
<221> NAME/KEY: MOD_RES
<222> LOCATION: (29)..(29)
<223> OTHER INFORMATION: Glutamic acid is protected by OtBu.

<400> SEQUENCE: 20

Gly Lys Pro Val Gly Lys Lys Arg Arg Pro Val Lys Val Tyr Pro Asn
1               5                   10                  15
Gly Ala Glu Asp Glu Ser Ala Glu Ala Phe Pro Leu Glu Phe
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (1)..(1)
<223> OTHER INFORMATION: Tryptophan is protected by Boc.
<220> FEATURE:
<221> NAME/KEY: MOD_RES
<222> LOCATION: (3)..(3)
<223> OTHER INFORMATION: Lysine is protected by Boc.
<220> FEATURE:
<221> NAME/KEY: MOD_RES
<222> LOCATION: (7)..(7)
<223> OTHER INFORMATION: Lysine is protected by Boc.
```

```
<220> FEATURE:
<221> NAME/KEY: MOD_RES
<222> LOCATION: (8)..(8)
<223> OTHER INFORMATION: Lysine is protected by Boc.
<220> FEATURE:
<221> NAME/KEY: MOD_RES
<222> LOCATION: (9)..(9)
<223> OTHER INFORMATION: Arginine is protected by Pbf.
<220> FEATURE:
<221> NAME/KEY: MOD_RES
<222> LOCATION: (10)..(10)
<223> OTHER INFORMATION: Arginine is protected by Pbf.
<220> FEATURE:
<221> NAME/KEY: MOD_RES
<222> LOCATION: (13)..(13)
<223> OTHER INFORMATION: Lysine is protected by Boc.
<220> FEATURE:
<221> NAME/KEY: MOD_RES
<222> LOCATION: (15)..(15)
<223> OTHER INFORMATION: Tyrosine is protected by tBu.
<220> FEATURE:
<221> NAME/KEY: MOD_RES
<222> LOCATION: (17)..(17)
<223> OTHER INFORMATION: Asparagine is protected by Trt.
<220> FEATURE:
<221> NAME/KEY: MOD_RES
<222> LOCATION: (20)..(20)
<223> OTHER INFORMATION: Glutamic acid is protected by OtBu.
<220> FEATURE:
<221> NAME/KEY: MOD_RES
<222> LOCATION: (21)..(21)
<223> OTHER INFORMATION: Aspartic acid is protected by OtBu.
<220> FEATURE:
<221> NAME/KEY: MOD_RES
<222> LOCATION: (22)..(22)
<223> OTHER INFORMATION: Glutamic acid is protected by OtBu.
<220> FEATURE:
<221> NAME/KEY: MOD_RES
<222> LOCATION: (23)..(23)
<223> OTHER INFORMATION: Serine is protected by tBu.
<220> FEATURE:
<221> NAME/KEY: MOD_RES
<222> LOCATION: (25)..(25)
<223> OTHER INFORMATION: Glutamic acid is protected by OtBu.
<220> FEATURE:
<221> NAME/KEY: MOD_RES
<222> LOCATION: (30)..(30)
<223> OTHER INFORMATION: Glutamic acid is protected by OtBu.

<400> SEQUENCE: 21

Trp Gly Lys Pro Val Gly Lys Arg Arg Pro Val Lys Val Tyr Pro
1               5                   10                  15

Asn Gly Ala Glu Asp Glu Ser Ala Glu Ala Phe Pro Leu Glu Phe
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (1)..(1)
<223> OTHER INFORMATION: Arginine is protected by Pbf.
<220> FEATURE:
<221> NAME/KEY: MOD_RES
<222> LOCATION: (2)..(2)
<223> OTHER INFORMATION: Tryptophan is protected by Boc.
<220> FEATURE:
<221> NAME/KEY: MOD_RES
<222> LOCATION: (4)..(4)
<223> OTHER INFORMATION: Lysine is protected by Boc.
<220> FEATURE:
<221> NAME/KEY: MOD_RES
<222> LOCATION: (8)..(8)
```

```
-continued

<223> OTHER INFORMATION: Lysine is protected by Boc.
<220> FEATURE:
<221> NAME/KEY: MOD_RES
<222> LOCATION: (9)..(9)
<223> OTHER INFORMATION: Lysine is protected by Boc.
<220> FEATURE:
<221> NAME/KEY: MOD_RES
<222> LOCATION: (10)..(10)
<223> OTHER INFORMATION: Arginine is protected by Pbf.
<220> FEATURE:
<221> NAME/KEY: MOD_RES
<222> LOCATION: (11)..(11)
<223> OTHER INFORMATION: Arginine is protected by Pbf.
<220> FEATURE:
<221> NAME/KEY: MOD_RES
<222> LOCATION: (14)..(14)
<223> OTHER INFORMATION: Lysine is protected by Boc.
<220> FEATURE:
<221> NAME/KEY: MOD_RES
<222> LOCATION: (16)..(16)
<223> OTHER INFORMATION: Tyrosine is protected by tBu.
<220> FEATURE:
<221> NAME/KEY: MOD_RES
<222> LOCATION: (18)..(18)
<223> OTHER INFORMATION: Asparagine is protected by Trt.
<220> FEATURE:
<221> NAME/KEY: MOD_RES
<222> LOCATION: (21)..(21)
<223> OTHER INFORMATION: Glutamic acid is protected by OtBu.
<220> FEATURE:
<221> NAME/KEY: MOD_RES
<222> LOCATION: (22)..(22)
<223> OTHER INFORMATION: Aspartic acid is protected by OtBu.
<220> FEATURE:
<221> NAME/KEY: MOD_RES
<222> LOCATION: (23)..(23)
<223> OTHER INFORMATION: Glutamic acid is protected by OtBu.
<220> FEATURE:
<221> NAME/KEY: MOD_RES
<222> LOCATION: (24)..(24)
<223> OTHER INFORMATION: Serine is protected by tBu.
<220> FEATURE:
<221> NAME/KEY: MOD_RES
<222> LOCATION: (26)..(26)
<223> OTHER INFORMATION: Glutamic acid is protected by OtBu.
<220> FEATURE:
<221> NAME/KEY: MOD_RES
<222> LOCATION: (31)..(31)
<223> OTHER INFORMATION: Glutamic acid is protected by OtBu.

<400> SEQUENCE: 22

Arg Trp Gly Lys Pro Val Gly Lys Lys Arg Arg Pro Val Lys Val Tyr
1               5                   10                  15

Pro Asn Gly Ala Glu Asp Glu Ser Ala Glu Ala Phe Pro Leu Glu Phe
            20                  25                  30

<210> SEQ ID NO 23
<211> LENGTH: 33
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (2)..(2)
<223> OTHER INFORMATION: Arginine is protected by Pbf.
<220> FEATURE:
<221> NAME/KEY: MOD_RES
<222> LOCATION: (3)..(3)
<223> OTHER INFORMATION: Tryptophan is protected by Boc.
<220> FEATURE:
<221> NAME/KEY: MOD_RES
<222> LOCATION: (5)..(5)
<223> OTHER INFORMATION: Lysine is protected by Boc.
<220> FEATURE:
<221> NAME/KEY: MOD_RES
```

```
<222> LOCATION: (9)..(9)
<223> OTHER INFORMATION: Lysine is protected by Boc.
<220> FEATURE:
<221> NAME/KEY: MOD_RES
<222> LOCATION: (10)..(10)
<223> OTHER INFORMATION: Lysine is protected by Boc.
<220> FEATURE:
<221> NAME/KEY: MOD_RES
<222> LOCATION: (11)..(11)
<223> OTHER INFORMATION: Arginine is protected by Pbf.
<220> FEATURE:
<221> NAME/KEY: MOD_RES
<222> LOCATION: (12)..(12)
<223> OTHER INFORMATION: Arginine is protected by Pbf.
<220> FEATURE:
<221> NAME/KEY: MOD_RES
<222> LOCATION: (15)..(15)
<223> OTHER INFORMATION: Lysine is protected by Boc.
<220> FEATURE:
<221> NAME/KEY: MOD_RES
<222> LOCATION: (17)..(17)
<223> OTHER INFORMATION: Tyrosine is protected by tBu.
<220> FEATURE:
<221> NAME/KEY: MOD_RES
<222> LOCATION: (19)..(19)
<223> OTHER INFORMATION: Asparagine is protected by Trt.
<220> FEATURE:
<221> NAME/KEY: MOD_RES
<222> LOCATION: (22)..(22)
<223> OTHER INFORMATION: Glutamic acid is protected by OtBu.
<220> FEATURE:
<221> NAME/KEY: MOD_RES
<222> LOCATION: (23)..(23)
<223> OTHER INFORMATION: Aspartic acid is protected by OtBu.
<220> FEATURE:
<221> NAME/KEY: MOD_RES
<222> LOCATION: (24)..(24)
<223> OTHER INFORMATION: Glutamic acid is protected by OtBu.
<220> FEATURE:
<221> NAME/KEY: MOD_RES
<222> LOCATION: (25)..(25)
<223> OTHER INFORMATION: Serine is protected by tBu.
<220> FEATURE:
<221> NAME/KEY: MOD_RES
<222> LOCATION: (27)..(27)
<223> OTHER INFORMATION: Glutamic acid is protected by OtBu.
<220> FEATURE:
<221> NAME/KEY: MOD_RES
<222> LOCATION: (32)..(32)
<223> OTHER INFORMATION: Glutamic acid is protected by OtBu.

<400> SEQUENCE: 23

Phe Arg Trp Gly Lys Pro Val Gly Lys Lys Arg Arg Pro Val Lys Val
1               5                   10                  15

Tyr Pro Asn Gly Ala Glu Asp Glu Ser Ala Glu Ala Phe Pro Leu Glu
            20                  25                  30

Phe

<210> SEQ ID NO 24
<211> LENGTH: 34
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (1)..(1)
<223> OTHER INFORMATION: Histidine is protected by Trt.
<220> FEATURE:
<221> NAME/KEY: MOD_RES
<222> LOCATION: (3)..(3)
<223> OTHER INFORMATION: Arginine is protected by Pbf.
<220> FEATURE:
<221> NAME/KEY: MOD_RES
<222> LOCATION: (4)..(4)
```

```
<223> OTHER INFORMATION: Tryptophan is protected by Boc.
<220> FEATURE:
<221> NAME/KEY: MOD_RES
<222> LOCATION: (6)..(6)
<223> OTHER INFORMATION: Lysine is protected by Boc.
<220> FEATURE:
<221> NAME/KEY: MOD_RES
<222> LOCATION: (10)..(10)
<223> OTHER INFORMATION: Lysine is protected by Boc.
<220> FEATURE:
<221> NAME/KEY: MOD_RES
<222> LOCATION: (11)..(11)
<223> OTHER INFORMATION: Lysine is protected by Boc.
<220> FEATURE:
<221> NAME/KEY: MOD_RES
<222> LOCATION: (12)..(12)
<223> OTHER INFORMATION: Arginine is protected by Pbf.
<220> FEATURE:
<221> NAME/KEY: MOD_RES
<222> LOCATION: (13)..(13)
<223> OTHER INFORMATION: Arginine is protected by Pbf.
<220> FEATURE:
<221> NAME/KEY: MOD_RES
<222> LOCATION: (16)..(16)
<223> OTHER INFORMATION: Lysine is protected by Boc.
<220> FEATURE:
<221> NAME/KEY: MOD_RES
<222> LOCATION: (18)..(18)
<223> OTHER INFORMATION: Tyrosine is protected by tBu.
<220> FEATURE:
<221> NAME/KEY: MOD_RES
<222> LOCATION: (20)..(20)
<223> OTHER INFORMATION: Asparagine is protected by Trt.
<220> FEATURE:
<221> NAME/KEY: MOD_RES
<222> LOCATION: (23)..(23)
<223> OTHER INFORMATION: Glutamic acid is protected by OtBu.
<220> FEATURE:
<221> NAME/KEY: MOD_RES
<222> LOCATION: (24)..(24)
<223> OTHER INFORMATION: Aspartic acid is protected by OtBu.
<220> FEATURE:
<221> NAME/KEY: MOD_RES
<222> LOCATION: (25)..(25)
<223> OTHER INFORMATION: Glutamic acid is protected by OtBu.
<220> FEATURE:
<221> NAME/KEY: MOD_RES
<222> LOCATION: (26)..(26)
<223> OTHER INFORMATION: Serine is protected by tBu.
<220> FEATURE:
<221> NAME/KEY: MOD_RES
<222> LOCATION: (28)..(28)
<223> OTHER INFORMATION: Glutamic acid is protected by OtBu.
<220> FEATURE:
<221> NAME/KEY: MOD_RES
<222> LOCATION: (33)..(33)
<223> OTHER INFORMATION: Glutamic acid is protected by OtBu.

<400> SEQUENCE: 24

His Phe Arg Trp Gly Lys Pro Val Gly Lys Lys Arg Arg Pro Val Lys
1               5                   10                  15

Val Tyr Pro Asn Gly Ala Glu Asp Glu Ser Ala Glu Ala Phe Pro Leu
            20                  25                  30

Glu Phe

<210> SEQ ID NO 25
<211> LENGTH: 35
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (1)..(1)
<223> OTHER INFORMATION: Glutamic acid is protected by OtBu.
```

```
<220> FEATURE:
<221> NAME/KEY: MOD_RES
<222> LOCATION: (2)..(2)
<223> OTHER INFORMATION: Histidine is protected by Trt.
<220> FEATURE:
<221> NAME/KEY: MOD_RES
<222> LOCATION: (4)..(4)
<223> OTHER INFORMATION: Arginine is protected by Pbf.
<220> FEATURE:
<221> NAME/KEY: MOD_RES
<222> LOCATION: (5)..(5)
<223> OTHER INFORMATION: Tryptophan is protected by Boc.
<220> FEATURE:
<221> NAME/KEY: MOD_RES
<222> LOCATION: (7)..(7)
<223> OTHER INFORMATION: Lysine is protected by Boc.
<220> FEATURE:
<221> NAME/KEY: MOD_RES
<222> LOCATION: (11)..(11)
<223> OTHER INFORMATION: Lysine is protected by Boc.
<220> FEATURE:
<221> NAME/KEY: MOD_RES
<222> LOCATION: (12)..(12)
<223> OTHER INFORMATION: Lysine is protected by Boc.
<220> FEATURE:
<221> NAME/KEY: MOD_RES
<222> LOCATION: (13)..(13)
<223> OTHER INFORMATION: Arginine is protected by Pbf.
<220> FEATURE:
<221> NAME/KEY: MOD_RES
<222> LOCATION: (14)..(14)
<223> OTHER INFORMATION: Arginine is protected by Pbf.
<220> FEATURE:
<221> NAME/KEY: MOD_RES
<222> LOCATION: (17)..(17)
<223> OTHER INFORMATION: Lysine is protected by Boc.
<220> FEATURE:
<221> NAME/KEY: MOD_RES
<222> LOCATION: (19)..(19)
<223> OTHER INFORMATION: Tyrosine is protected by tBu.
<220> FEATURE:
<221> NAME/KEY: MOD_RES
<222> LOCATION: (21)..(21)
<223> OTHER INFORMATION: Asparagine is protected by Trt.
<220> FEATURE:
<221> NAME/KEY: MOD_RES
<222> LOCATION: (24)..(24)
<223> OTHER INFORMATION: Glutamic acid is protected by OtBu.
<220> FEATURE:
<221> NAME/KEY: MOD_RES
<222> LOCATION: (25)..(25)
<223> OTHER INFORMATION: Aspartic acid is protected by OtBu.
<220> FEATURE:
<221> NAME/KEY: MOD_RES
<222> LOCATION: (26)..(26)
<223> OTHER INFORMATION: Glutamic acid is protected by OtBu.
<220> FEATURE:
<221> NAME/KEY: MOD_RES
<222> LOCATION: (27)..(27)
<223> OTHER INFORMATION: Serine is protected by tBu.
<220> FEATURE:
<221> NAME/KEY: MOD_RES
<222> LOCATION: (29)..(29)
<223> OTHER INFORMATION: Glutamic acid is protected by OtBu.
<220> FEATURE:
<221> NAME/KEY: MOD_RES
<222> LOCATION: (34)..(34)
<223> OTHER INFORMATION: Glutamic acid is protected by OtBu.

<400> SEQUENCE: 25

Glu His Phe Arg Trp Gly Lys Pro Val Gly Lys Lys Arg Arg Pro Val
1               5                   10                  15

Lys Val Tyr Pro Asn Gly Ala Glu Asp Glu Ser Ala Glu Ala Phe Pro
            20                  25                  30

Leu Glu Phe
        35
```

```
<210> SEQ ID NO 26
<211> LENGTH: 36
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (2)..(2)
<223> OTHER INFORMATION: Glutamic acid is protected by OtBu.
<220> FEATURE:
<221> NAME/KEY: MOD_RES
<222> LOCATION: (3)..(3)
<223> OTHER INFORMATION: Histidine is protected by Trt.
<220> FEATURE:
<221> NAME/KEY: MOD_RES
<222> LOCATION: (5)..(5)
<223> OTHER INFORMATION: Arginine is protected by Pbf.
<220> FEATURE:
<221> NAME/KEY: MOD_RES
<222> LOCATION: (6)..(6)
<223> OTHER INFORMATION: Tryptophan is protected by Boc.
<220> FEATURE:
<221> NAME/KEY: MOD_RES
<222> LOCATION: (8)..(8)
<223> OTHER INFORMATION: Lysine is protected by Boc.
<220> FEATURE:
<221> NAME/KEY: MOD_RES
<222> LOCATION: (12)..(12)
<223> OTHER INFORMATION: Lysine is protected by Boc.
<220> FEATURE:
<221> NAME/KEY: MOD_RES
<222> LOCATION: (13)..(13)
<223> OTHER INFORMATION: Lysine is protected by Boc.
<220> FEATURE:
<221> NAME/KEY: MOD_RES
<222> LOCATION: (14)..(14)
<223> OTHER INFORMATION: Arginine is protected by Pbf.
<220> FEATURE:
<221> NAME/KEY: MOD_RES
<222> LOCATION: (15)..(15)
<223> OTHER INFORMATION: Arginine is protected by Pbf.
<220> FEATURE:
<221> NAME/KEY: MOD_RES
<222> LOCATION: (18)..(18)
<223> OTHER INFORMATION: Lysine is protected by Boc.
<220> FEATURE:
<221> NAME/KEY: MOD_RES
<222> LOCATION: (20)..(20)
<223> OTHER INFORMATION: Tyrosine is protected by tBu.
<220> FEATURE:
<221> NAME/KEY: MOD_RES
<222> LOCATION: (22)..(22)
<223> OTHER INFORMATION: Asparagine is protected by Trt.
<220> FEATURE:
<221> NAME/KEY: MOD_RES
<222> LOCATION: (25)..(25)
<223> OTHER INFORMATION: Glutamic acid is protected by OtBu.
<220> FEATURE:
<221> NAME/KEY: MOD_RES
<222> LOCATION: (26)..(26)
<223> OTHER INFORMATION: Aspartic acid is protected by OtBu.
<220> FEATURE:
<221> NAME/KEY: MOD_RES
<222> LOCATION: (27)..(27)
<223> OTHER INFORMATION: Glutamic acid is protected by OtBu.
<220> FEATURE:
<221> NAME/KEY: MOD_RES
<222> LOCATION: (28)..(28)
<223> OTHER INFORMATION: Serine is protected by tBu.
<220> FEATURE:
<221> NAME/KEY: MOD_RES
<222> LOCATION: (30)..(30)
<223> OTHER INFORMATION: Glutamic acid is protected by OtBu.
<220> FEATURE:
<221> NAME/KEY: MOD_RES
<222> LOCATION: (35)..(35)
```

<223> OTHER INFORMATION: Glutamic acid is protected by OtBu.

<400> SEQUENCE: 26

Met Glu His Phe Arg Trp Gly Lys Pro Val Gly Lys Lys Arg Arg Pro
1               5                   10                  15

Val Lys Val Tyr Pro Asn Gly Ala Glu Asp Glu Ser Ala Glu Ala Phe
            20                  25                  30

Pro Leu Glu Phe
        35

<210> SEQ ID NO 27
<211> LENGTH: 37
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (1)..(1)
<223> OTHER INFORMATION: Serine is protected by tBu.
<220> FEATURE:
<221> NAME/KEY: MOD_RES
<222> LOCATION: (3)..(3)
<223> OTHER INFORMATION: Glutamic acid is protected by OtBu.
<220> FEATURE:
<221> NAME/KEY: MOD_RES
<222> LOCATION: (4)..(4)
<223> OTHER INFORMATION: Histidine is protected by Trt.
<220> FEATURE:
<221> NAME/KEY: MOD_RES
<222> LOCATION: (6)..(6)
<223> OTHER INFORMATION: Arginine is protected by Pbf.
<220> FEATURE:
<221> NAME/KEY: MOD_RES
<222> LOCATION: (7)..(7)
<223> OTHER INFORMATION: Tryptophan is protected by Boc.
<220> FEATURE:
<221> NAME/KEY: MOD_RES
<222> LOCATION: (9)..(9)
<223> OTHER INFORMATION: Lysine is protected by Boc.
<220> FEATURE:
<221> NAME/KEY: MOD_RES
<222> LOCATION: (13)..(13)
<223> OTHER INFORMATION: Lysine is protected by Boc.
<220> FEATURE:
<221> NAME/KEY: MOD_RES
<222> LOCATION: (14)..(14)
<223> OTHER INFORMATION: Lysine is protected by Boc.
<220> FEATURE:
<221> NAME/KEY: MOD_RES
<222> LOCATION: (15)..(15)
<223> OTHER INFORMATION: Arginine is protected by Pbf.
<220> FEATURE:
<221> NAME/KEY: MOD_RES
<222> LOCATION: (16)..(16)
<223> OTHER INFORMATION: Arginine is protected by Pbf.
<220> FEATURE:
<221> NAME/KEY: MOD_RES
<222> LOCATION: (19)..(19)
<223> OTHER INFORMATION: Lysine is protected by Boc.
<220> FEATURE:
<221> NAME/KEY: MOD_RES
<222> LOCATION: (21)..(21)
<223> OTHER INFORMATION: Tyrosine is protected by tBu.
<220> FEATURE:
<221> NAME/KEY: MOD_RES
<222> LOCATION: (23)..(23)
<223> OTHER INFORMATION: Asparagine is protected by Trt.
<220> FEATURE:
<221> NAME/KEY: MOD_RES
<222> LOCATION: (26)..(26)
<223> OTHER INFORMATION: Glutamic acid is protected by OtBu.
<220> FEATURE:
<221> NAME/KEY: MOD_RES
<222> LOCATION: (27)..(27)

```
<223> OTHER INFORMATION: Aspartic acid is protected by OtBu.
<220> FEATURE:
<221> NAME/KEY: MOD_RES
<222> LOCATION: (28)..(28)
<223> OTHER INFORMATION: Glutamic acid is protected by OtBu.
<220> FEATURE:
<221> NAME/KEY: MOD_RES
<222> LOCATION: (29)..(29)
<223> OTHER INFORMATION: Serine is protected by tBu.
<220> FEATURE:
<221> NAME/KEY: MOD_RES
<222> LOCATION: (31)..(31)
<223> OTHER INFORMATION: Glutamic acid is protected by OtBu.
<220> FEATURE:
<221> NAME/KEY: MOD_RES
<222> LOCATION: (36)..(36)
<223> OTHER INFORMATION: Glutamic acid is protected by OtBu.

<400> SEQUENCE: 27

Ser Met Glu His Phe Arg Trp Gly Lys Pro Val Gly Lys Lys Arg Arg
1               5                   10                  15

Pro Val Lys Val Tyr Pro Asn Gly Ala Glu Asp Glu Ser Ala Glu Ala
            20                  25                  30

Phe Pro Leu Glu Phe
        35

<210> SEQ ID NO 28
<211> LENGTH: 38
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (1)..(1)
<223> OTHER INFORMATION: Tyrosine is protected by tBu.
<220> FEATURE:
<221> NAME/KEY: MOD_RES
<222> LOCATION: (2)..(2)
<223> OTHER INFORMATION: Serine is protected by tBu.
<220> FEATURE:
<221> NAME/KEY: MOD_RES
<222> LOCATION: (4)..(4)
<223> OTHER INFORMATION: Glutamic acid is protected by OtBu.
<220> FEATURE:
<221> NAME/KEY: MOD_RES
<222> LOCATION: (5)..(5)
<223> OTHER INFORMATION: Histidine is protected by Trt.
<220> FEATURE:
<221> NAME/KEY: MOD_RES
<222> LOCATION: (7)..(7)
<223> OTHER INFORMATION: Arginine is protected by Pbf.
<220> FEATURE:
<221> NAME/KEY: MOD_RES
<222> LOCATION: (8)..(8)
<223> OTHER INFORMATION: Tryptophan is protected by Boc.
<220> FEATURE:
<221> NAME/KEY: MOD_RES
<222> LOCATION: (10)..(10)
<223> OTHER INFORMATION: Lysine is protected by Boc.
<220> FEATURE:
<221> NAME/KEY: MOD_RES
<222> LOCATION: (14)..(14)
<223> OTHER INFORMATION: Lysine is protected by Boc.
<220> FEATURE:
<221> NAME/KEY: MOD_RES
<222> LOCATION: (15)..(15)
<223> OTHER INFORMATION: Lysine is protected by Boc.
<220> FEATURE:
<221> NAME/KEY: MOD_RES
<222> LOCATION: (16)..(16)
<223> OTHER INFORMATION: Arginine is protected by Pbf.
<220> FEATURE:
<221> NAME/KEY: MOD_RES
<222> LOCATION: (17)..(17)
```

```
<223> OTHER INFORMATION: Arginine is protected by Pbf.
<220> FEATURE:
<221> NAME/KEY: MOD_RES
<222> LOCATION: (20)..(20)
<223> OTHER INFORMATION: Lysine is protected by Boc.
<220> FEATURE:
<221> NAME/KEY: MOD_RES
<222> LOCATION: (22)..(22)
<223> OTHER INFORMATION: Tyrosine is protected by tBu.
<220> FEATURE:
<221> NAME/KEY: MOD_RES
<222> LOCATION: (24)..(24)
<223> OTHER INFORMATION: Asparagine is protected by Trt.
<220> FEATURE:
<221> NAME/KEY: MOD_RES
<222> LOCATION: (27)..(27)
<223> OTHER INFORMATION: Glutamic acid is protected by OtBu.
<220> FEATURE:
<221> NAME/KEY: MOD_RES
<222> LOCATION: (28)..(28)
<223> OTHER INFORMATION: Aspartic acid is protected by OtBu.
<220> FEATURE:
<221> NAME/KEY: MOD_RES
<222> LOCATION: (29)..(29)
<223> OTHER INFORMATION: Glutamic acid is protected by OtBu.
<220> FEATURE:
<221> NAME/KEY: MOD_RES
<222> LOCATION: (30)..(30)
<223> OTHER INFORMATION: Serine is protected by tBu.
<220> FEATURE:
<221> NAME/KEY: MOD_RES
<222> LOCATION: (32)..(32)
<223> OTHER INFORMATION: Glutamic acid is protected by OtBu.
<220> FEATURE:
<221> NAME/KEY: MOD_RES
<222> LOCATION: (37)..(37)
<223> OTHER INFORMATION: Glutamic acid is protected by OtBu.

<400> SEQUENCE: 28

Tyr Ser Met Glu His Phe Arg Trp Gly Lys Pro Val Gly Lys Lys Arg
1               5                   10                  15

Arg Pro Val Lys Val Tyr Pro Asn Gly Ala Glu Asp Glu Ser Ala Glu
            20                  25                  30

Ala Phe Pro Leu Glu Phe
        35

<210> SEQ ID NO 29
<211> LENGTH: 39
<212> TYPE: PRT
<213> ORGANISM: Artificial Sequence
<220> FEATURE:
<223> OTHER INFORMATION: The sequence is synthesized
<220> FEATURE:
<221> NAME/KEY: MOD_RES
<222> LOCATION: (1)..(1)
<223> OTHER INFORMATION: Serine is protected by tBu.
<220> FEATURE:
<221> NAME/KEY: MOD_RES
<222> LOCATION: (2)..(2)
<223> OTHER INFORMATION: Tyrosine is protected by tBu.
<220> FEATURE:
<221> NAME/KEY: MOD_RES
<222> LOCATION: (3)..(3)
<223> OTHER INFORMATION: Serine is protected by tBu.
<220> FEATURE:
<221> NAME/KEY: MOD_RES
<222> LOCATION: (5)..(5)
<223> OTHER INFORMATION: Glutamic acid is protected by OtBu.
<220> FEATURE:
<221> NAME/KEY: MOD_RES
<222> LOCATION: (6)..(6)
<223> OTHER INFORMATION: Histidine is protected by Trt.
<220> FEATURE:
<221> NAME/KEY: MOD_RES
<222> LOCATION: (8)..(8)
```

```
<223> OTHER INFORMATION: Arginine is protected by Pbf.
<220> FEATURE:
<221> NAME/KEY: MOD_RES
<222> LOCATION: (9)..(9)
<223> OTHER INFORMATION: Tryptophan is protected by Boc.
<220> FEATURE:
<221> NAME/KEY: MOD_RES
<222> LOCATION: (11)..(11)
<223> OTHER INFORMATION: Lysine is protected by Boc.
<220> FEATURE:
<221> NAME/KEY: MOD_RES
<222> LOCATION: (15)..(15)
<223> OTHER INFORMATION: Lysine is protected by Boc.
<220> FEATURE:
<221> NAME/KEY: MOD_RES
<222> LOCATION: (16)..(16)
<223> OTHER INFORMATION: Lysine is protected by Boc.
<220> FEATURE:
<221> NAME/KEY: MOD_RES
<222> LOCATION: (17)..(17)
<223> OTHER INFORMATION: Arginine is protected by Pbf.
<220> FEATURE:
<221> NAME/KEY: MOD_RES
<222> LOCATION: (18)..(18)
<223> OTHER INFORMATION: Arginine is protected by Pbf.
<220> FEATURE:
<221> NAME/KEY: MOD_RES
<222> LOCATION: (21)..(21)
<223> OTHER INFORMATION: Lysine is protected by Boc.
<220> FEATURE:
<221> NAME/KEY: MOD_RES
<222> LOCATION: (23)..(23)
<223> OTHER INFORMATION: Tyrosine is protected by tBu.
<220> FEATURE:
<221> NAME/KEY: MOD_RES
<222> LOCATION: (25)..(25)
<223> OTHER INFORMATION: Asparagine is protected by Trt.
<220> FEATURE:
<221> NAME/KEY: MOD_RES
<222> LOCATION: (28)..(28)
<223> OTHER INFORMATION: Glutamic acid is protected by OtBu.
<220> FEATURE:
<221> NAME/KEY: MOD_RES
<222> LOCATION: (29)..(29)
<223> OTHER INFORMATION: Aspartic acid is protected by OtBu.
<220> FEATURE:
<221> NAME/KEY: MOD_RES
<222> LOCATION: (30)..(30)
<223> OTHER INFORMATION: Glutamic acid is protected by OtBu.
<220> FEATURE:
<221> NAME/KEY: MOD_RES
<222> LOCATION: (31)..(31)
<223> OTHER INFORMATION: Serine is protected by tBu.
<220> FEATURE:
<221> NAME/KEY: MOD_RES
<222> LOCATION: (33)..(33)
<223> OTHER INFORMATION: Glutamic acid is protected by OtBu.
<220> FEATURE:
<221> NAME/KEY: MOD_RES
<222> LOCATION: (38)..(38)
<223> OTHER INFORMATION: Glutamic acid is protected by OtBu.

<400> SEQUENCE: 29

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu Phe
        35
```